US006310093B1

(12) United States Patent
Newcomb

(10) Patent No.: US 6,310,093 B1
(45) Date of Patent: Oct. 30, 2001

(54) METHOD OF PREVENTING NEURONAL DEATH

(75) Inventor: Robert Newcomb, Palo Alto, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/141,881

(22) Filed: Aug. 27, 1998

Related U.S. Application Data

(60) Provisional application No. 60/057,220, filed on Aug. 29, 1997.

(51) Int. Cl.$^7$ .......................... A61K 31/195; A01N 55/06
(52) U.S. Cl. .......................... 514/496; 514/492; 514/561
(58) Field of Search .................... 514/496, 492, 514/561; 556/125

(56) References Cited

U.S. PATENT DOCUMENTS

| | | | |
|---|---|---|---|
| 5,158,976 | 10/1992 | Rosenberg | 514/561 |
| 5,378,455 | 1/1995 | Kealey et al. | 424/73 |
| 5,552,427 | 9/1996 | Matsutani et al. | 514/398 |

OTHER PUBLICATIONS

Joseph et al. European Journal of Biochemistry, 119/3 523–529, Feb. 1981.*
Aledo et al. Biochimica et Biophysica Acta, 1323, No. 2, pp. 173–184, Feb. 1997.*
Newcomb, R. et al Journal of Biological Chemistry, 272, No. 17, pp. 11276–11282, May 1997.*
Database Medline, DN 88276318. Steinberg,G. et al. Neuroscience Lett., 89, 193–197, Jan. 1988.*
Dawson Jr., R. and Wallace, D.R., "Regulation of Phosphate–Activated Glutaminase (PAG) by Glutamate Analogues" *Neurochemical Research* 18 (2) :125–132 (1993).
Kisner, D.L., et al., "The rediscovery of DON (6–diazo–5–oxo–L–norleucine)" *Recent Results Cancer Res* 74:258–63 (1980) (abstract only).

Brockman, R.W., et al., "Mode of action of azotomycin" Antimicrob. Ag. Chemother. vol. date 1969:56–62 (1970) (abstract only).
International Search Report based on PCT Application No. US98/17968.
Ahluwalia, G.S., et al., "Metabolism and Action of Amino Acid Analog Anti–Cancer Agents,"Pharma. Ther. 46: 243–271 (1990).
Higashiguchi, Takahi, et al., "Protein synthesis in isolated enterocytes from septic or endotoxaemic rats: regulation by glutamine," Clinical Science 89: 311–319 (1995).
Huber, K.R., et al., "Uptake of Glutamine Antimetabolites 6–Diazo–5–Oxo–Norleucine (Don) and Acivicin in Sensitive and Resistant Tumor Cells," Int. J. Cancer 41: 752–755 (1988).
Kaneko, T., et al., "Enhancement of Glutaminase–Like Immunoreactivity in Rat Brain by an Irreversible Inhibitor of the Enzyme," Brain Res. Bulletin 28: 897–907 (1992).
Kvamme, E. et al., "The Effect of Acetyl–Coenzyme A on Phosphate–Activated Glutaminase from Pig Kidney and Brain," Biochem. J. 137:525–530 (1974).
Shapiro, Richard A., et al., "Inactivation of Rat Renal Phosphate–dependent Glutaminase with 6–Diazo–5–oxo–L–norleucine," The Journal of Biological Chemistry 254(8): 2835–2838 (1979).
Shapiro, Richard A., et al., "Covalent Interaction of L–2–Amino–4oxo–5–chloropentanoic Acid with Rat Renal Phosphate–dependent Glutaminase," The Journal of Biological Chemistry 253(19):7086–7090 (1978).

* cited by examiner

Primary Examiner—Michael Borin
(74) Attorney, Agent, or Firm—LeeAnn Gorthey

(57) ABSTRACT

Disclosed is a method for preventing neuronal cell death subsequent to an injury to neuronal tissue, particularly central nervous tissue exposed to an ischemic or hypoxic event, to trauma or to a chronic neurodegenerative disorder. The method includes exposing the cells to a glutaminase inhibitor that is relatively impermeant to healthy, intact cell membranes, and which is preferably a specific inhibitor of the form of glutaminase that is widely present in brain tissue.

16 Claims, 4 Drawing Sheets

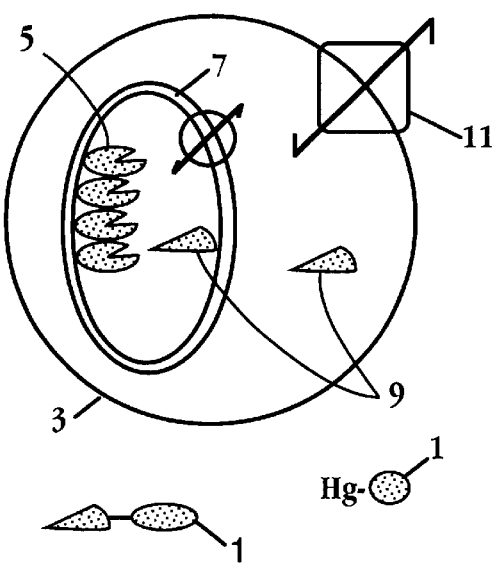
Fig 5A
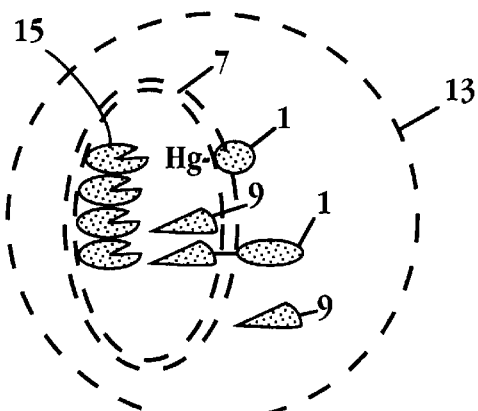
Fig 5B
Inhibitor Properties
| | |
|---|---|
| Hg-⊙ | Membrane impermeant reagent (i.e., pCMPS) |
| ◁–◯ | Membrane impermeant inhibitor |
| ◁ | Selective glutaminase inhibitor nonselective for transport systems (membrane permeable) |
Fig 5C

METHOD OF PREVENTING NEURONAL DEATH

The present application claims priority to U.S. provisional application having Ser. No. 60/057,220, filed Aug. 29, 1997, which is hereby incorporated by reference.

The invention described herein was made under SBIR Grant No. 1-R43 NS 35406-01 awarded by the National Institute of Neurological Disorders and Stroke (NINDS). Accordingly, the U.S. Government may have certain rights in the invention.

FIELD OF THE INVENTION

The invention is concerned with a treatment method for preventing neuronal death subsequent to injury, particularly in the central nervous system.

REFERENCES

Ahiuwalia, G. S. et al, "Metabolism and action of amino acid analog anti-cancer agents", Pharmac. Ther. 46: 243–271 (1990).

Almeida, A. F. et al., "Maximal activities of key enzymes of glutaminolysis, glycolysis, krebs cycle and pentose-phosphate pathway of several tissues in mature and aged rats,", Int. J. Biochem. 21: 937–940 (1989).

Chung-Bok, M-I. et al, "Rat hepatic glutaminase: identification of the full coding sequence and characterization of a functional promoter", Biochem. J. 324: 193–200 (1997).

Curthoys, N. P. et al., "Regulation of glutaminase activity and glutamine metabolism", Ann. Rev. Nutr. 15: 133–159 (1995). Dugan, L. L. et al., "Glia modulate the response of murine cortical neurons to excitotoxicity: Glia exacerbate AMPA neurotoxicity", J. Neurosci. 15: 4545–4555 (1995).

Drejer, J. et al., Exp. Brain Res. 47, 259–269 (1982).

Godfrey, S. et al., "Correlation between activation and dimer formation of rat renal phosphate-dependent glutaminase", J. Biol. Chem. 252: 1927–1931 (1977).

Hertz, L. et al., Neurochem. Res. 3, 1–14 (1978).

Hogstad, S. et al., "Glutaminase in neurons and astrocytes cultured from mouse brain: Kinetic properties and effects of phosphate, glutamate, and ammonia", Neurochem. Res. 13: 383–388 (1988).

Huber, K. R. et al., "Uptake of glutamine antimetabolites 6-diazo-5-oxo-L-norleucine (DON) and acivicin in sensitive and resistant tumor cell lines", Int. J. Cancer 41: 752–755 (1988).

Kaneko, T. et al., "Enhancement of glutaminase-like immunoreactivity by an irreversible inhibitor of the enzyme", Brain. Res. Bul. 28: 897–907 (1992).

Kvamme, E. et al., Biochem. J. 137: 525–30 (1974).

Kvamme, E. et al., "Glutaminase from mammalian tissue", Meth. Enzymol. 113: 241–256 (1985).

Kovacevic, Z. et al., "Mitochondrial metabolism of glutamine and glutamate and its physiological significance", Physiological Reviews 63,: 547–605 (1983).

Lo, E. H. et al., "Temporal correlation analysis of penumbral dynamics in focal cerebral ischemia", J. Cereb. Blood. Flow Metab. 16: 60–68 (1996).

Matsumoto, K. et al., "Secondary elevation of extracellular neurotransmitter amino acids in the reperfusion phase following focal cerebral ischemia", J. Cereb. Blood Flow Metab. 16: 114–124 (1996).

Newcomb, R. et al., J. Biol. Chem. 272: 11276–82 (1997).

Roberts, D. V., Enzyme Kinetics, Cambridge University Press, Cambridge, pp 23–30 (1977).

Rosenberg, P. A, "Accumulation of extracellular glutamate and neuronal death in astrocyte-poor cortical cultures exposed to glutamine", Glia 4: 91–100 (1991).

Shapiro, R. A. et al., "Covalent interaction of L-2-amino-4-oxo-5-chloropentanoic acid with rat renal phosphate-dependent glutaminase" J. Biol. Chem. 253: 7086–7090 (1978).

Shapiro, R. A. et al., Arch. Biochem. Biophys. 243: 1–7 (1985).

Shaw, E., Adv. Enzymol. 63: 271–347 (1989).

Zea Longa, E. et al., "Reversible middle artery occlusion without craniectomy", Stroke 20: 84–91 (1989).

BACKGROUND OF THE INVENTION

High extracellular levels of glutamate have been recognized as a significant biochemical consequence of various forms of neuronal injury, including ischemic, degenerative and traumatic brain damage. Further, it has been proposed that the elevated glutamate levels exacerbate the primary insult, possibly by acting at excitatory glutamate receptors. While it was previously believed that the source of the excess glutamate was neuronal stores, it is now recognized that at least some of the glutamate may be the result of enzymatic conversion of glutamine to glutamate by glutaminase.

U.S. Pat. No. 5,158,976 (Rosenberg) discloses the general idea of blocking glutaminase for neuroprotection, but does not appreciate the advantages of using membrane impermeant compounds, as described herein. The approach described by Rosenberg is directed to inhibiting intracellular glutamine metabolism and production of glutamate and does not appreciate that most of the extra glutamate in damaged neuronal tissue is produced by a glutaminase activity that is exposed to the extracellular milieu, presumably as a result of cell damage, as described herein. While Rosenberg describes the systemic toxicity that can ensue when glutaminase is inhibited systemically, it does not appreciate that such toxicity can be reduced considerably by selecting a glutaminase inhibitor that is impermeant to cell membranes and, preferably, specific for the mitochondrial form of the enzyme present in neuronal cells.

According to the discoveries underlying the present invention, membrane impermeant inhibitors having certain characteristics defined herein are both neuroprotective and selectively inhibit glutamate production by damaged neurons. Glutaminase in intact neurons, as well as glutamatergic transmission, are unaffected by such inhibitors, reducing systemic side effects and toxicity.

SUMMARY OF THE INVENTION

In one aspect, the invention concerns a method of reducing damage to neuronal cells in a neuronal tissue of a subject who has experienced neuronal injury. The method includes administering a compound capable of selectively inhibiting extracellular glutaminase relative to glutaminase present in intact cells. Preferably, the selective inhibition of glutaminase is characterized by the compound's inability to permeate intact cell membranes, as evidenced by an inability of said compound to inhibit glutaminase when contacted with live primary cell cultures of neurons and glia and an ability to inhibit glutaminase when applied to crude membranes derived from said cell cultures.

In a preferred embodiment, the invention is directed to treatment of neuronal injury in the central nervous system.

Such injury includes, but is not limited to, ischemic injury, such as focal ischemia due to stroke, traumatic injury that is the result of trauma, and chronic degenerative damage to the brain, such as from Alzheimer's disease.

Preferably, the compound comprises a reactive portion having a chemical affinity for the active site of glutaminase. The reactive portion is preferably a thiol-reactive moiety, as in the compound p-(chloromercuri)phenylsulfonic acid. Such compounds also include glutamate analogs; particularly preferred analogs are derived from 4fluoroglutamate. The compound may further include a bulky and/or polar portion effective to inhibit passage of the compound through cell membranes.

In another embodiment, a preferred compound has at least one anionic or highly polar group, selected from a nitro group, a carboxylate, and an oxide of sulfur or phosphorus. Of such compounds, those preferred are those which exhibit less inhibition of glutaminase in the presence of increased levels of phosphate, and which do not activate glutaminase in the presence of increased levels of phosphate. Particularly preferred compounds of this class have a significantly hydrophobic portion, such as an aromatic group or alkyl chain, preferably having at least six carbon atoms. Also preferred are those compounds which are gem-disubstituted with two such polar or anionic groups. In one embodiment, the compound has a gem-dinitro group, such as 1,1-dinitrooctane.

In another preferred embodiment, the method of the invention uses a compound which is further characterized by an inhibition potency that results in inhibition of at least 50% of extracellular glutaminase measured in the nerve tissue sample when the compound is present in the tissue at a concentration of less than 1 mM for a time period less than about 1 hour. In yet another embodiment, the compound is further characterized by having a selectivity for brain/kidney glutaminase. Selectivity, in this sense, indicates that the compound inhibits the brain/kidney glutaminase by 50% at a concentration that is no more than $\frac{1}{10}$ the concentration at which it inhibits or interferes with the function of other glutamine-utilizing enzymes, such as glutamine amidotransferases and γ-glutamyl transpeptidase.

With respect to administration, the compound can be administered either before, during or after the injurious event. In preferred embodiments of the invention, it is appreciated that the compound can be administered more than 2 hours following the event. The compound is preferably still efficacious when administered 6, 12, 18 or even 24 hours following the injury. According to an important feature of the invention, the compound can be administered by any of a number of parenteral routes, including intravenous, intraarterial, intrathecal, intracerebroventricular and the like. It is appreciated that the compound is able to cross the damaged blood brain barrier after neuronal injury.

In a related aspect, the invention includes a method for screening for neuroprotective compounds. The method is predicated on the observation that useful compounds cannot permeate or are highly resistant to permeation of intact neuronal membranes, but inhibit the glutaminase enzyme present in the membranes of damaged or injured cells. In view of these observations, compounds are tested in a glutaminase reaction mixture that consists essentially of membranes, particularly mitochondrial membranes derived from central nervous tissue. The reaction mixture also includes about a half-saturating amount of glutamine, usually greater than 0.1 mM, and a glutaminase-activating concentration of phosphate (generally greater than about 0.5 mM). Glutaminase activity in the system is compared in the presence and absence of the test compound, and the compound is selected for use in neuroprotection if the compound (i) inhibits glutamate production in the membrane preparation relative to control, and (ii) does not inhibit glutamate production in an intact cell preparation. The compound is tested in the intact cell membrane preparation by adding it to the cells at a concentration of between about 0.1 and 2 mM, washing the cells, and then damaging the cells and measuring glutaminase activity.

The method may comprise further steps of (i) exposing live neurons to the compound, (ii) measuring glutamate production in the culture medium, and (iii) selecting the compound if it does not inhibit glutamate production by the live neurons, relative to neurons which have not been exposed to the compound. Alternatively, further testing may comprise (i) measuring glutamatergic transmission in hippocampal brain slices exposed to the compound, and (ii) selecting the compound if it shows no effect on the field potential at a concentration equal to or greater than that required to inhibit glutaminase in neuronal cultures which have damaged, for example, by exposure to about 2 mM glutamine. These Further steps are especially useful if the compound is suspected to be a reversible in inhibitor of glutaminase.

These and other objects and features of the invention will become more fully apparent when the following detailed description of the invention is read in conjunction with the accompanying drawings.

BRIEF DESCRIPTION OF THE FIGURES

FIGS. 5A–5C show a schematic diagram of the ability of various types of glutaminase inhibitor to access mitochondria glutaminase in intact (5A) and injured (5B) cells;

DETAILED DESCRIPTION OF THE INVENTION

Figure 1:
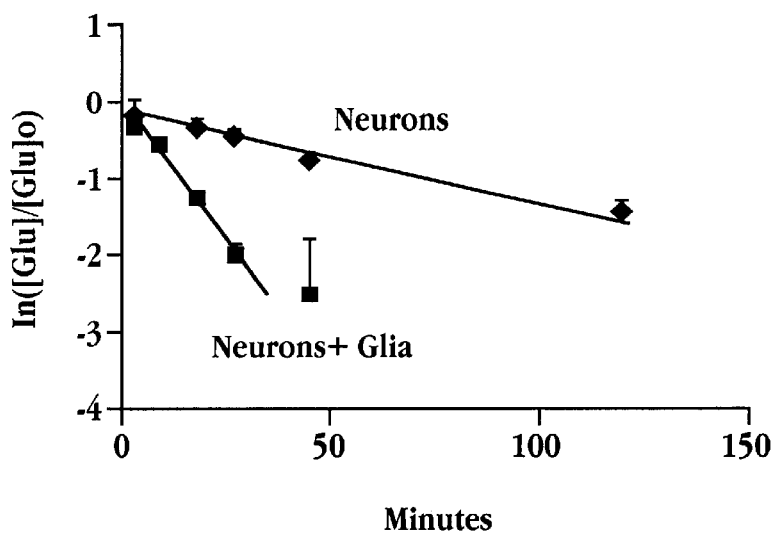
FIG. 1 shows a plot of clearance of medium glutamate by intact cultures of neuronal and mixed glial-neuronal cells.

The present invention particularly concerns the biochemical events that surround neuronal damage, particularly as may occur in the brain as a result of cerebral ischemia, trauma, or degeneration. For example, parts of the brain may be damaged as the result of deprivation of blood flow during and after what is commonly referred to as "stroke." This condition (focal ischemia) may occur when one or more of the cerebral arteries is occluded by a thromboembolus or when there is a hemorrhage of one or more of the cerebral arteries. The brain, as well as other parts of the central nervous system, can also be damaged when deprived of blood flow as a result of cardiac arrest (global ischemia). Other sources of damage to central nervous tissue include, but are not limited to, concussive trauma to the brain or spinal cord, and degenerative conditions, such as Alzheimer's disease. Methods described herein can be used in the diagnosis and/or treatment of any conditions that include damage of neuronal tissue. The invention should not be limited to the conditions mentioned above or exemplified below.

Depending on its duration, cessation of blood flow to all or part of the central nervous system (CNS) results in neuronal death in the affected areas. In the case of focal ischemia, cell death will center in the region deprived of blood; in the case of global ischemia, cell death may be focused in those areas of the brain that are most susceptible or vulnerable to insult.

Following ischemic insult or other traumatic injury that results in breakage of neuronal cells, a number of biochemical changes occur in neuronal tissue surrounding the injured region. Particularly relevant to the present invention, there is a rise in the extracellular concentration of the excitatory neurotransmitter glutamate. According to one theory, the high concentration of glutamate is an important factor in the phenomenon known as "delayed neuronal death", in which the ischemic lesion increases approximately 2-fold over a period of time 2–72 hours following the initial ischemic insult.

While it has been observed that the amount of glutamate measured in dialysates of damaged brain regions is higher than can be accounted for by the normal release of neurotransmitter stores from glutamatergic nerve terminals involved, the precise source of the extra glutamate has not heretofore been identified. It is a discovery of the present invention that the rise in glutamate, particularly as measured about 24 hours following ischemia, is due in significant part to conversion of glutamine to glutamate by the enzyme glutaminase. This effect was observed in vitro, as described below, and is predicted to occur in vivo. More particularly, it is a discovery of the present invention that the inner mitochondrial membranes derived from damaged or broken cells are a source of significant glutamate after neuronal damage.

This observation forms the basis for the present invention. That is, it is a further discovery of the present invention that inhibition of the glutaminase exposed as a result of cell damage is useful in protecting against further neuronal damage. Hence, according to the present invention, neuroprotection can be achieved by selectively inhibiting the extracellular glutaminase that is exposed as a result of the injury. Selectivity of inhibition is important, since selective inhibition of glutaminase in damaged cells avoids interference with glutamatergic transmission and glutamine metabolism, as demonstrated herein. More particularly, the present invention is based on the observation that membrane impermeant glutaminase inhibitor compounds are effective in preventing death of neuronal cells in a mixture of cells in which cell breakage has occurred. Membrane impermeant inhibitory molecules are advantageous because they inhibit only glutaminase enzyme molecules that are exposed to the extracellular space and are therefore considerably less toxic to living cells than are freely permeable inhibitors. In the sections below are described methods for selecting such membrane impermeant inhibitors, as well as methods for testing their effectiveness in preventing neuronal death.

I. Definitions

The terms "neuronal cell damage", "damage to neuronal cells", and "cell injury" refer to conditions in which the integrity of a neuronal cell has been compromised. This condition may be a result of an ischemic event, a concussive traumatic event, a degenerative event, or the like. Damage to cells may be induced in vitro by various methods, such as freezing and thawing, exposing to hypoxic conditions, or treatment with the glutamate receptor agonist NMDA.

The terms "hypoxic", "hypoxia", "ischemic" and "ischemia", as used herein, refer to conditions in which eukaryotic cells, particularly neuronal cells, are exposed to oxygen concentrations that are at least 50% less than a normal range of oxygen tension required for normal growth and maintenance of such cells in culture or in vivo.

By "membrane impermeant", with respect to a glutaminase inhibitor, is meant that a compound is effective to inhibit extracellular glutaminase at a concentration that at least 10 times less than a concentration at which it inhibits glutaminase in intact cells.

The terms "extracellular glutaminase" and "exposed glutaminase" are used herein to refer to the location of the enzymatic activity of the enzyme with respect to the cells from which it is derived. While intracellular glutaminase generally does not rapidly hydrolyze glutamine added to the culture medium of intact cells, when such glutaminase is exposed to the extracellular milieu, such as by injury to the cell outer membrane, it becomes "extracellular" in that it is then able hydrolyze exogenously added glutamine.

A "glutaminase inhibitor" is a compound which, when added to an enzyme that exhibits glutaminase activity, reduces the activity of the enzyme. Preferably, the enzyme activity is reduced by at least about 50% within about one hour when exposed to a concentration of 1 mM or less of inhibitor. Alternatively, the term refers to compounds that reduce by at least 50% the ability of the enzyme to convert glutamine to glutamate, when tested in the presence of a half saturating concentration of glutamine, under the above conditions.

The "active site of glutaminase" is the site of the enzyme which recognizes the substrate (glutamine); compounds which competitively inhibit the enzyme also bind at this site. These compounds include glutamate analogs and are expected to include thiol reactive compounds, which react with an essential thiol.

A compound "derived from" an active glutaminase inhibitor, as defined herein, is a compound that has been modified enhance selectivity and/or to impart or increase membrane impermeability, e.g. by addition of a bully and/or polar substituent, without significantly impairing the activity of the inhibitor.

An "oxide of sulfur or phosphorus" includes such groups as sulfate, sulfonate, sulfone, sulfoxide, sulfite, sulfinate, phosphate, phosphonate, pyrophosphate, and alkoxy or aryloxy esters of such compounds.

II. Membrane Impermeant Glutaminase Inhibitors
A. Glutaminase Activity in Nervous Tissue This section describes glutaminase activity as it has been characterized in central nervous tissue. This description particularly illuminates what is meant by selective glutaminase inhibition in the context of the present invention.

Mammals typically express two isoforms of the mitochondrial enzyme glutaminase (Curthoys). The liver isoform is expressed only in adult liver tissue, whereas brain/kidney glutaminase is expressed at high levels in brain, kidney, intestine, the cells of the immune system, and in many transformed cells. The two isoforms are the products of distinct, but structurally related genes (Chung-Bok).

Glutaminase is currently recognized as the most significant glutamine utilizing enzyme present in mammalian central nervous tissue (e.g., the brain and spinal cord). The enzyme is highly compartmentalized and is present in higher abundance in neurons than glia (Hogstad). It is also associated with the inner mitochondrial membrane (Curthoys). The enzyme catalyzes the following reaction:

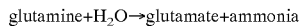

glutamine+$H_2O$→glutamate+ammonia

Both of the products of the glutaminase reaction, glutamate and ammonia, are highly neurotoxic, and it has not been established whether one or both of these products are responsible for cellular damage.

Mitochondrial glutaminase is activated by phosphate, which is present at a concentration of 2–5 mM in brain tissue and in the cerebrospinal fluid (CSF) that bathes the brain and spinal cord. The maximal activity of glutaminase in brain is 5–10 $\mu$mol/min/g (Alameida et al., 1989). This translates to a capacity for generating glutamate at a concentration of 5–10 mM each minute; a rate far in excess of the 5–10 $\mu$M $IC_{50}$ for toxicity of glutamate on isolated neurons (Rosenberg; Dugan et al., 1995). Therefore, it is apparent that only a very minor fraction of the glutaminase present in brain needs to be active in a pathological circumstance in order to cause damage.

Glutamine, the substrate for glutaminase, is present in mammalian brain extracellular fluid at the highest concentration relative to other amino acids (500 $\mu$M in rabbit CSF; Matsumoto et al., 1996). These concentrations are well within the range of optimal catalytic activity of the glutaminase enzyme (Km=2–8 mM glutamine, Kovacevic and McGiven, 1983).

Glutamine concentrations in brain extracellular dialysates remain elevated following focal ischemic insult to brain tissue. Extracellular (dialysate) glutamine remains high for at least 6 h of reperfusion after 2 h focal cerebral ischemia (Lo et al., 1995). The presumed source of this glutamine is glial cells, which have an active uptake mechanism for glutamate. This glutamate is then converted to glutamine in the cells and subsequently exported into the extracellular fluid.

B. Inhibitors of Glutaminase

There are no known inhibitors that are both potent and specific for the brain/kidney form of glutamine. Rather, known inhibitors also inhibit a variety of glutamine utilizing enzymes. These compounds include L2-amino4-oxo-5-chloropentanoic acid ("chloroketone"; Shapiro et al. 1978) and 6-diazo-5-oxo-L-norleucine ("DON"; Shapiro et al. 1979). The latter compound is one of several known antiglutamine antimetabolites isolated from yeast (Ahluwalia et al. 1990). Other antiglutamine antimetabolites, such as acivicin and azaserine, do not inhibit glutaminase.

U.S. Pat. No. 5,158,976 lists a number of compounds that may be glutaminase inhibitors. The inhibitor DON, as noted above, is not selective for glutaminase, and inhibits other glutamine-utilizing enzymes such as amidotransferases. In general, amino acid antiglutamine antimetabolites such as DON readily cross cell membranes (Huber), most likely by carrier systems for neutral amino acids.

In contrast, preferred compounds used in the present method are membrane impermeable and/or selective for extracellular glutaminase, as discussed herein.

C. Measuring Glutaminase Activity

C1. General Principles

Glutaminase activity can be monitored by detecting production of either of the products of the reaction, glutamate or ammonia. Generally, glutamate production is measured, since ammonia is a product of any of a number of biological reactions.

Glutamate production can be measured by any of a number of standard methods known in the art, including, but not limited to, chemical and chromatographic detection methods and coupled enzyme assays that utilize NADH and glutamate dehydrogenase. Extracellular glutamate concentrations can also be measured in vivo, using microdialysis methods known in the art. One suitable method for measuring glutamate is a microtiter-based two-step assay in which glutamate formed in the initial step is quantitatively deaminated by glutamate dehydrogenase to yield an equivalent amount of NADH (Godfrey et al., 1977; Kvamme et al., 1985), which can then be detected spectrophotometrically.

In experiments carried out in support of the present invention, as detailed in Example 2, a chemical detection method was used to monitor glutamate production in culture media. Briefly, the medium was collected at various times and in response to specific stimuli, and was frozen at −80° C. prior to assay. The glutamate in the sample was derivatized with o-phthaldialdehyde and either 2-mercaptoethanol or N-acetyl-L-cysteine) to form detectable products, followed by separation and analysis by HPLC, according to known methods.

Experiments on the clearance of glutamate from culture medium showed first order kinetics in intact glial, neuronal, and mixed cultures. This allows expression of medium glutamate concentrations as:

$$d[Glu]/dt = S - k[Glu] \quad (1)$$

where [Glu], in units of $\mu$M, is the concentration of glutamate in the 0.4 ml of medium in a culture well, S (in $\mu$M/min) is the rate of addition of glutamate to the culture medium from cellular sources, and k (in $min^{-1}$) is the empirically determined rate constant for clearance (Roberts). Pseudo-first order kinetics are expected for the clearance of glutamate at concentrations significantly below the Km for cellular uptake (about 45 $\mu$M; Hertz; Drejer). Although the value of k is proportional to cell (carrier) density, little variation is expected in cultures containing glia, as glial cultures are confluent.

In cultures where glutamate concentrations are (within error) constant, d[Glu]/dt is close to zero, and cellular production of medium glutamate is balanced by its removal, such that glutamate production can be calculated from the steady state equation:

$$S = k[Glu] \quad (2)$$

Calculations were performed using the slopes of the regression lines which describe the rate constants for glutamate removal (FIG. 1) and the mean values for culture medium glutamate concentrations. Because of the relevance to data on glutamate toxicity, rates of glutamate production are given with units of concentration over time. For comparative purposes, glutamate production rates are also provided as pmol of glutamate produced per min in each culture. These values were obtained after multiplication by the volume of culture medium.

These calculations form the basis for measuring glutaminase activity in cultures or tissues containing intact and damaged or broken nerve cells and for determining relative glutaminase inhibitory activities in the context of the present invention.

As mentioned above, the substrate for glutaminase, glutamine, is the amino acid present in highest concentration in the brain extracellular fluid (500 μM in rabbit CSF, Matsumoto et al., 1996), and glutamine is also present in high concentration in bulk tissue (4–8 mM; Clarke et al., 1989). These concentrations are well within the range of optimal catalytic activity of the enzyme ($K_m$=2–8 mM glutamine; Kovacevic and McGiven, 1983).

C2. Glutamate Production in Neuronal Cultures

Experiments carried out in support of the present invention demonstrated that the steady state concentration of glutamate in the medium of neuronal culture was 0.38±0.05 μM. The clearance of glutamate from the medium of intact neuronal cultures could be described by a first order process with an apparent kinetic constant of 0.0012 $min^{-1}$. Thus the intact neuronal cultures exhibit a relatively slow rate of glutamate uptake. Further experiments revealed the time course of appearance of glutamate in the cell culture medium of intact pure neuronal cultures or of cultures lysed by a freeze-thaw cycle, both in the presence and absence of 2 mM glutamine. In the absence of added glutamine, glutamate concentrations in intact neuronal cultures are maintained at below 1 μM. Under these conditions, the rate of glutamate production calculated from the steady state equation is 0.0046 μM/min (1.8 pmol/min). Thus, the production of glutamate by neurons cultured in the absence of added glutamine is also very slow and is small in comparison to the total cellular content of glutamate.

Figure 2A:
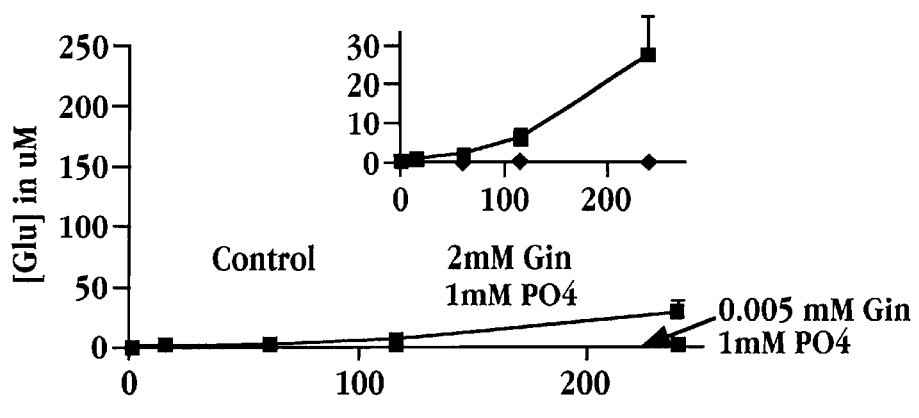
FIGS. 2A and 2B show plots of glutamate production by cultures of intact cells (2A) and cells damaged by freezing and thawing (2B) in the absence and presence of added glutamine (2 mM), as indicated.
Figure 2B:
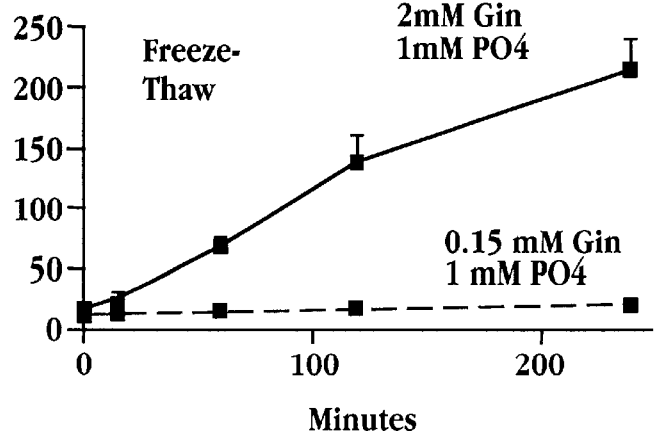

When 2 mM glutamine is added to intact neuronal cultures, the rate at which glutamate accumulates in the culture medium increases with time (FIG. 2). Since the clearance of medium glutamate by neuronal cultures is extremely slow, one estimate of the rate of glutamate production by neurons exposed to glutamine can be obtained from the initial rate of glutamate accumulation. Using the difference in glutamate concentrations at 1 and 15 min after glutamine addition, a value of 0.032±0.006 μM/min (12.8 pmol/min) was obtained. Since glutamine exposure itself eventually causes neuronal death and high rates of glutamine hydrolysis, this estimate of glutamate production should be viewed as an upper limit. However, this value is similar to that obtained by comparing glutamate production by glial and mixed neuronal-glial cultures exposed to glutamate (see below).

In contrast, the rate of glutamate production by damaged cultures of pure neurons exposed to glutamine was found to be very rapid, and was linear with time. In the absence of added glutamine (i.e., in the 0.15 mM glutamine manufactured by the neuronal cultures), glutamate production into the medium of cultures lysed by freezing and thawing occurred at a rate of 0.035±0.006 μM/min (14 pmol/min). However, the addition of 2 mM glutamine to the medium of freeze-thawed cultures resulted in the much higher rate of glutamate production of 0.79±0.08 μM/min (316 pmol/min). Similarly, neuronal cultures which were subjected to "excitotoxic" injury by treatment for 5 h with 500 μM of the glutamate receptor agonist N-methyl-D-aspartate (NMDA) and then incubated with 2 mM glutamine produced glutamate in the culture medium at a rate of 0.54±0.09 μM/min (216 pmol/min). Thus, damaged neurons incubated in 2 mM glutamine produce within 6–8 min an amount equal to that released by freeze-thawing. The various rates and rate constants measured with neuronal cultures are summarized in Table 1.

TABLE 1

Glutamate uptake and production by intact and damaged neuronal cultures

| Culture | Glutamate uptake (k) min-1 | Glutamate concentration μM | Glutamate production (S) μM/min |
|---|---|---|---|
| Intact neurons | | | |
| 0.005 mM Gln | 0.012 | 0.38 ± 0.05 (s.e.m. n = 8) | 0.0046 |
| 2 mM Gln | | increases exponentially | 0.032 ± 0.006 (8) |
| Damaged neurons | | | |
| Freeze-thaw | | | |
| 0.15 mM Gln | | increases linearly | 0.035 ± 0.006 (8) |
| 2 mM Gln | | increases linearly | 0.79 ± 0.08 (8) |
| NMDA treated | | | |
| 0.15 mM Gln | | increases linearly | 0.020 ± 0.013 (8)* |
| 2 mM Gln | | increases linearly | 0.54 ± 0.09 (8) |

*calculated from the initial rate of accumulation

C3. Glutamate Production in Glial Cultures

It was found that pure cultures of intact astrocytes, when incubated with 15 μM glutamate, exhibit a rapid uptake of glutamate that is described by a first order rate constant of 0.083 $min^{-1}$. This shows that uptake of glutamate by the glial cultures is about 7 times faster than that of the neuronal cultures. The glutamate concentration of glial cultures was maintained below 1 μM when cells were maintained in the absence or presence of 2 mM added glutamine or when subjected to hypoxic conditions (see below). The medium glutamate concentration remained unchanged between 7 and 24 h after medium change and was 0.14±0.04 μM and 0.36±0.06 μM in medium containing 0.15 mM or 2.0 mM glutamine, respectively. Based on these steady state concentrations and the measured rate of glutamate uptake, the rates of glutamate production in the absence and presence of added glutamine were calculated to be 0.012 μM/min (4.8 pmol/min) and 0.030 μM/min (12 pmol/min), respectively. Thus, the calculated rates of glutamate production by glial cultures are only slightly affected by the addition of glutamine and are similar to those observed in intact neurons cultured in the absence of added glutamine. The various rates and rate constants measured for cultures of pure glial cells are summarized in Table 2.

TABLE 2

Glutamate uptake and production in intact glial and mixed glial-neuronal cultures

| Culture | Glutamate uptake (k) | Glutamate concentration | Glutamate production (S) |
|---|---|---|---|
| Glial | | | |
| 0.15 mM Gln | 0.083 | 0.14 ± 0.04 (10) | 0.012 |
| 2 mM Gln | | 0.36 ± 0.06 (10) | 0.03 |
| Glial-neuronal | | | |
| 0.15 mM Gln | 0.072 | 0.37 ± 0.06 (25) | 0.027 |
| 2 mM Gln | | 0.83 ± 0.47 (20) | 0.06 |

C4. Glutamate Production in Mixed Glial-neuronal Cultures

Added glutamate (15 μM) was rapidly cleared from the medium of the mixed glial-neuronal cultures (FIG. 1). The uptake again fit to a first order process and occurred with a rate constant of 0.072 min$^{-1}$. The observed rate constant suggests that the glial cells constitute the primary site of glutamate uptake in the mixed cultures. When the intact mixed cultures were maintained in the absence or presence of added 2 mM glutamine, they also maintained steady state concentrations of glutamate below 1 $\mu$M (0.37±0.06 $\mu$M and 0.83±0.47 $\mu$M respectively). Thus, from the steady state equation, the rates of glutamate production were estimated to be 0.027 $\mu$M/min (11 pmol/min) in the absence of added glutamine and 0.060 $\mu$M/min (24 pmol/min) in the presence of 2 mM glutamine. The various kinetic constants measured for intact glial-neuronal cultures are summarized in Table 2.

Glutamate production by intact neurons exposed to glutamine can be estimated from the difference in the steady state rates of glutamate production by glial and mixed glial-neuronal cultures exposed to glutamine. This value of 0.030 $\mu$M/min (12 pmol/min) agrees well with the initial rate of production of glutamate by pure neuronal cultures exposed to glutamine (above).

The results obtained in the above-described experiments demonstrate that glutamate production by damaged neurons exposed to the brain concentration of glutamine (2 mM) is 10–30 fold greater than that by intact neurons or glia. The amount of glutamate released subsequent to cell death was also measured. Although measurable amounts of glutamate were released by freeze-thaw of neuronal cultures (4.5±0.5 $\mu$M, or 1.8 nmol total in 400 $\mu$l culture volume, s.e.m. n=8), the amount released was only equal to that produced by 6–8 min of glutaminase activity following neuronal death. The concentration of glutamate released into cell cultures medium by depolarization of mixed neuronal/glial cultures by treatment for 5 min with 80 mM potassium was 0.01±0.007 $\mu$M (or 4 pmol, s.e.m. n=6), which is only a small fraction of glutamate production by damaged neurons, even if glial uptake is considered.

C5. Glutamate Production after Neuronal Death is Attributable to Glutaminase Activity Experiments described in Part C2, above, showed glutamate production from glutamine by damaged neurons to be the most significant source of glutamate in primary cultures of mouse neocortex. Subsequent experiments demonstrated that this glutamate production was due to glutamine hydrolysis catalyzed by mitochondrial glutaminase present in the mitochondrial membranes derived from dead or dying cells, and exposed to the extracellular, glutamine substrate-containing fluid as a result of the dying process.

Figure 3:
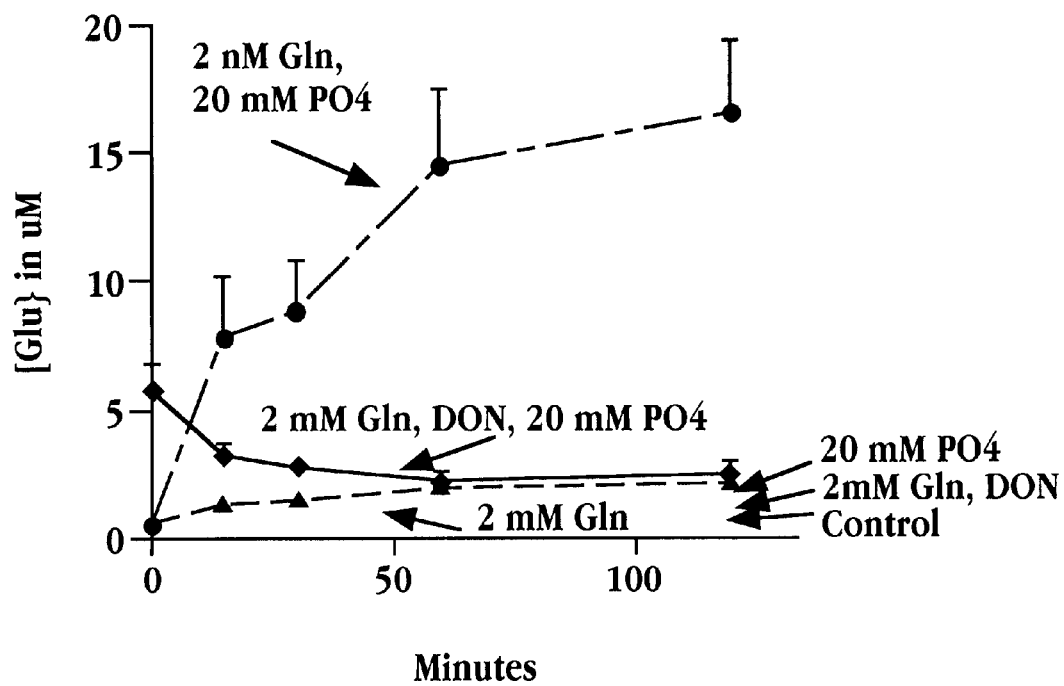
FIG. 3 shows the time course of glutamate production in the medium of mixed neuronal-glial cultures after selective neuronal damage by treatment with NMDA.

As described above, mitochondrial glutaminase is characterized by activation by phosphate and is inhibited by contact with the glutamine affinity labeling reagent DON. FIG. 3 illustrates the time course of accumulation of glutamate in mixed neuronal-glial cultures incubated in a phosphate free saline following selective damage of neurons by pretreatment with 500 $\mu$M NMDA for five hours, as described in Example 3. As shown, glutamate generation was dependent on the presence of added 2 mM glutamine, and increased 8-fold by the inclusion of 20 mM phosphate. The addition of 2 mM DON contributes about 5 $\mu$M glutamate as a contaminant, which is removed by glial uptake. The added DON inhibited 90% of the glutamate production observed in the presence of 2 mM glutamine and 20 mM phosphate. In contrast, DON inhibited only 50% of the lower amount of glutamate production observed in the absence of added phosphate.

Further experiments in support of the present invention also showed that the increased glutamate generating activity which follows neuronal death is inhibited by L-2-amino4-oxo-chloropentanoic acid. This profile of activation and inhibition is that which is expected for the brain/kidney glutaminase (Kvamme, 1994, Curthoys and Watford, 1995); the activation by phosphate is unique to glutaminase. Further experiments demonstrated that 2 mM acivicin, an inhibitor of gamma-glutamyl transpeptidase (which is present in low abundance in brain, and also has glutaminase activity) and glutamine amidotransferases, had no effect on glutamine hydrolysis by damaged neurons. Likewise, 2 mM glutamate-$\gamma$-hydrazide, an inhibitor of the liver isoform of glutaminase, had no effect on glutamine hydrolysis in the system.

Figure 4:
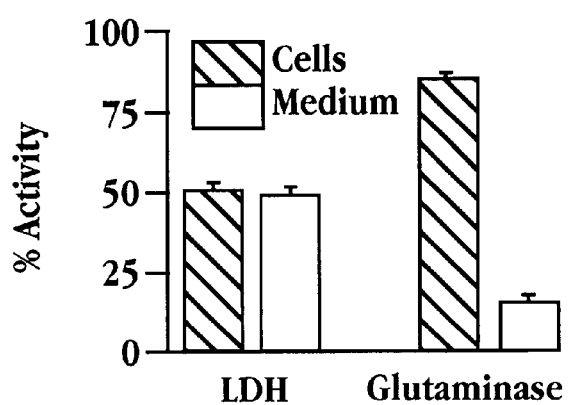
FIG. 4 shows a plot of lactate dehydrogenase activity localization in neuronal cell membranes with and without NMDA treatment.

Cellular glutaminase is closely associated with the inner mitochondrial membrane. Additional experiments carried out in support of the present invention revealed that glutamine hydrolysis activity remains associated with cell fragments after neuronal death. Briefly, as detailed in Examples 3 and 4, neuronal cultures were exposed to N-methyl-D-aspartate (NMDA) for a period of time sufficient to kill the cells. The cells were then pelleted, and glutaminase and LDH activities were measured in culture media and cellular pellet. Results are shown in FIG. 4. While the LDH activity was equally distributed between the two fractions, glutaminase activity remained associated with the pelleted cell fragments. Further Western blot experiments using an antiglutaminase antibody confirmed this finding. That is, following cell death, the glutaminase immunoreactivity remained in the particulate fractions.

It was concluded that glutamate generation by damaged neurons has properties of the brain/kidney glutaminase, and not of other candidate enzymes. The identical inhibitor/activator profile was obtained with crude brain membranes, suggesting that this conclusion is not unique to the particular culture system.

Further experiments carried out in support of the present invention revealed that glutamate generation by glutaminase in damaged neurons was sufficient to account for glutamine toxicity in hypoxic neuronal/glial cells. Measurements of glutamate and glutamine concentrations, as well as of the release of the cytoplasmic marker enzyme, lactate dehydrogenase (LDH), were made with the medium of mixed neuronal-astrocyte cultures exposed to hypoxic and control conditions, with and without the addition of 2 mM glutamine. For comparative purposes, the measurements were made in mixed cultures in which complete neuronal death was caused by a 5h exposure to 500 $\mu$M NMDA. The first glutamate measurement was made at the end of hypoxia (5h with mixed cultures, 7h with astrocytes), and the second at 19 h after the subsequent return of oxygen. If added, glutamine was present during and after hypoxia. LDH released by the experimental treatment was measured at 24 h, and is expressed as a percentage of the total cellular content (neurons in mixed cultures, and glia in glial cultures). To verify the neuronal origin of LDH and glutamate, similar experiments were performed on cultures that only contained glia. These data are summarized in Table 3.

TABLE 3

Glutamate and glutamine in cultures exposed to hypoxia or NMDA

| Condition | time (h) | Glu ($\mu$M) | Gln (mM) | % cell death (LDH) |
|---|---|---|---|---|
| Mixed Cultures | | | | |
| Control | 5 | 0.37 ± 0.06 (n = 25) | 0.16 ± 0.004 (4) | |
| | 24 | 0.34 ± 0.02 (4) | | 13.7 ± 1.7 (25) |
| 2 mM Gln | 5 | 0.83 ± 0.47 | 2.1 ± 0.22 (4) | |
| | 24 | | | 17.6 ± 2.9 (23) |
| Hypoxia | 5 | 0.3 ± 0.04 (22) | 0.06 ± 0.005 (4) | |
| | 24 | 2.17 ± 0.27 (20) | 0.31 ± 0.04 (4) | 26.5 ± 2.7 (21) |
| Hypoxia 2 mM Gln | 5 | 3.1 ± 0.28 (21) | 2.3 ± 0.1 (4) | |
| | 24 | 3.88 ± 0.14 (25) | | 42.2 + −3.1 (23) |
| NMDA 2 mM Gln | 2–4 | 7.0 ± 0.6 (16) | | 100 |
| Gial Cultures | | | | |
| Hypoxia | 7 | 0.11 ± 0.09 (10) | 0.06 ± 0.007 (6) | |
| | 24 | 0.11 ± 0.02 (10) | 0.19 ± 0.008 (6) | <2–5 |
| Hypoxia 2 mM Gln | 7 | 0.39 ± .09 (10) | 2.0 ± 0.16 (6) | |
| | 24 | 0.39 ± 0.07 (10) | 2.5 ± 0.16 (6) | <2–5 |

The combination of glutamine and hypoxia generates medium glutamate concentrations of 3–4 $\mu$M. This is near the $IC_{50}$ value for toxicity of glutamate in neuronal cultures (Rosenberg, 1991, Dugan et al. 1995), and sufficient to account for the approximate doubling of neuronal death (to 40%) which is caused by the addition of 2 MM glutamine. The use NMDA to induce complete neuronal death in the mixed cultures resulted in a steady state glutamate concentration of 7 $\mu$M. On the basis of these data, it is concluded that glutamate generation in these cultures is proportional to the amount of neuronal death. Since glutamate generation by damaged neurons behaved as expected for the glutaminase, it is concluded that the activity of the glutaminase in damaged neurons can account for the generation of toxic amounts of glutamate in mixed neuron-astrocyte cultures exposed to glutamine and hypoxia. Glucose is present in the these experiments, and glial uptake of glutamate was not affected by the exposure to hypoxia or glutamine.

D. Selective Glutaminase-Inhibiting Compounds

Glutaminase is inhibited by known compounds which also inhibit a variety of other glutamine utilizing enzymes. Such compounds include L-2-amino-4-oxo-5-chloropentanoic acid ("chloroketone"; Shapiro et al., 1978) and 6-diazo-5-oxo-L-norleucine ("DON", Shapiro et al., 1979). The latter compound is one of several antiglutamine antimetabolites isolated from yeast. These compounds, including the chloroketone, are only weak (mM) inhibitors. Moreover, they exhibit variable selectivity for glutamine-utilizing enzymes and are not generally membrane impermeant in the context of the present invention. For example, acivicin and azaserine inhibit a number of enzymes with related activities, and have been studied as anti-tumor compounds, but they do not inhibit glutaminase. Both DON and acivicin readily cross cell membranes (Huber). In contrast, glutaminase inhibitors in accordance with the present invention are characterized by the ability to selectively inhibit extracellular or exposed glutaminase relative to glutaminase present inside intact cells, or, more generally, impermeability to intact cell membranes.

In selecting inhibitor compounds for use in the present methods, candidate compounds are first tested for toxicity in primary neuronal-glial cultures, for example, by determining whether they cause release of LDH by the cells into the medium, as described in Example 3. (LDH is a standard indicator of lack of cell integrity). Nontoxic inhibitors are further tested for ability to inhibit glutaminase activity. Example 5 describes a glutaminase inhibition assay carried out in a homogenized brain membrane suspension.

Those compounds which show activity comparable or superior to glutamate are modified, if necessary, at a region of the molecule remote from the reactive site, to impart or increase membrane impermeability. The term "membrane impermeability" is related to the phenomenon of selective inhibition, defined below. Operationally, it means that a compound is effective to inhibit extracellular glutaminase at much lower concentrations than the concentration at which it shows comparable inhibition of glutaminase or other glutamate-utilizing enzymes in intact cells. In the present context "much lower" may be considered to indicate a 10-fold concentration differential. By "selective inhibition" of extracellular or exposed glutaminase is meant that the compound is not able to inhibit glutaminase when applied to intact, healthy neuronal cells, but that, when applied to damaged cells, it is able to inhibit a glutaminase fraction that is exposed to the extracellular medium or, more precisely, a glutaminase fraction that is not separated from the extracellular milieu by an intact cell membrane. By way of example, the membrane impermeable inhibitor pCMPS selectively inhibits exposed glutaminase, while at much higher concentrations it blocks glial uptake of glutamate.

Inhibition in intact and traumatized cell cultures is compared, using methods described in Example 2, and compounds are selected for further consideration if they selectively inhibit glutaminase activity in traumatized cells, or cell membranes derived from such traumatized cells, vs. intact cells. A compound that inhibits glutaminase irreversibly and is selective for traumatized membranes will, given a fixed time of incubation (for example, 15 minutes), inhibit glutaminase activity present in such membranes by at least 50% at a concentration that is no more than $\frac{1}{10}$ of its $IC_{50}$ for glutaminase in intact cells (e.g., a concentration at which it inhibits glutaminase in intact cells by 50%). More preferably, the ratio will be $\frac{1}{50}$, and even more preferably $\frac{1}{100}$ or less the concentration at which it affects intracellular glutaminase activity.

The advantage of selective membrane permeability can be appreciated when combined with the discovery of the present invention, as described in Part C above, that most of the harmful products (glutamate and/or ammonia) produced in the extracellular fluid of damaged tissue are generated by glutaminase that is extracellular or which has contact with the extracellular milieu by virtue of the initial traumatic event.

In view of the selectivity that can be achieved by the compartmentalization of enzyme activity and the inability of inhibitors of the present invention to gain access to intact cell interiors, it is appreciated that it is not necessary that the inhibitory compound be absolutely selective for the glutaminase enzyme; however, it is preferable. In general, it would be expected that useful therapeutics in accordance with the present invention will inhibit the mitochondrial brain/kidney glutaminase described herein by at least 50% at a concentration of compound that is ineffective in inhibiting other glutamine-utilizing enzymes present in the cells, e.g., γ-glutamyltranspeptidase or glutamine-amidotransferase.

As described above, glutamate generation by glutaminase in damaged neurons was shown to correlate with glutamine toxicity in hypoxic neuronal/glial cells. Accordingly, further testing for neuroprotective activity in vitro and in vivo models of hypoxic and ischemic neuronal damage is carried out on positive candidate compounds, e.g., those that are found to be membrane impermeant glutaminase inhibitors. This aspect of the invention is discussed in Section III, below.

Membrane impermeability ensures that the drug will have its primary activity in the extracellular fluid, where, as discussed above, most of the harmful glutaminase activity occurs. FIG. 5 is a diagram that illustrates this point by comparing the relative accessibility of membrane-permeant and membrane-impermeant inhibitors in healthy (Panel A) and damaged (Panel B) cells. Membrane impermeant compound 1, illustrated as a solid triangle linked to a solid circle, is unable to pass through the healthy cell membrane 3 and therefore cannot interact with or inhibit the glutaminase enzyme 5 (illustrated as closed circular symbols with indented wedges) which is located on the inner surface of the mitochondrial membranes 7. In contrast, a membrane permeable compound 9 (illustrated as a solid triangular wedge) is able to cross the membranes, either by diffusion or via a transporter 11, and interact with glutaminase 5.

FIG. 5B illustrates the situation in damaged cells. Cell membrane 13 is leaky or absent so that both membrane impermeant compounds 1 and membrane permeant compounds 9 can interact with glutaminase 15. In the context of the present invention this glutaminase can be considered to be "extracellular glutaminase", since it is exposed to and obtains substrate glutamine from the extracellular fluids.

One class of compounds effective as membrane impermeant glutaminase inhibitors may be represented generally by the drawing shown at 1 in FIG. 5. The first portion (represented by a wedge) has a chemical affinity towards the active site of glutaminase. This portion may be, for example, a thiol reactive moiety such as mercury, N-ethyl maleimide, etc. The compound may be a glutamate analog, preferably modified at the side chain carboxyl group to confer enhanced reactivity, as shown by the 4-fluoro compound, below. Also included as possible modifying groups are those known to inhibit enzymes which utilize cysteine residues to hydrolyze amide bonds (Shaw, 1989); these include aldehydes and ketones, particularly chloromethyl, fluoromethyl, and trifluoromethyl ketones, sulfonium salts, nitriles, diazoketones (such as 6-diazo-5-oxo-L-norleucine derivatives), diazomethylketones, hydroxamates, alkenes, and alkynes.

Modification at other sites of the molecule, e.g. at the amino group or carbons C2 and C3, can be used to modify selectivity of binding or membrane impermeability. In particular, the inhibitor compound may include a group which imparts or enhances membrane impermeability. This group, represented in FIG. 5 by a circle, is preferably connected by a spacer group to the reactive portion of the compound, so as to maintain access of the reactive portion (i.e. the modified side chain carboxyl region) to the active site of glutaminase. A bulky and/or a highly polar, preferably charged, group can be used to enhance membrane impermeability. For example, in pCMPS (p-(chloromercuri) phenyl sulfonate), an aromatic ring links a sulfonic acid group to the reactive (mercuric) center. Other suitable charged groups include carboxylates, other inorganic acid salts (e.g. sulfates, phosphonates) or protonated amines.

For compounds whose activity is based on recognition of substrate (i.e. competitive inhibitors, such as reactive glutamine analogs), attachment of the bulky and/or polar group should not interfere with substrate binding to the enzyme. The effect of various structural modification of glutamate analogs on binding can be evaluated by glutaminase inhibition assays, such as those described herein.

Table 4 summarizes the effect of various glutamate analogs on the glutaminase activity of homogenized rat brain membranes, as described in Example 5. With the exception of glycyl-4-fluoroglutamate, prepared as described below, the compounds were obtained form commercial suppliers, as indicated in the Table.

Under the assay conditions employed (i.e. concentrations of the substrate, glutamine, and activator, phosphate, near half maximal effects), glutamate, a known inhibitor, had no significant effect on enzyme activity at 3.3 mM. Several of the analogs shown had potency greater than that of glutamate. In particular, a 500 μM concentration of 4-fluoroglutamate gave half maximal inhibition of glutaminase. Several compounds having methyl substitution at the 2- and 3- positions showed moderate inhibition, as did several compounds with amino group substitutions (e.g. Asp-Glu-OH, n-acetyl-Asp-Glu, carbobenzoxy-Glu-OH, acetyl-DL-Glu-OH, and (±)-erythro-3-methylglutamate). A compound having multiple modifications, glycyl-4-fluoroglutamate, prepared as described in Example 9, inhibited glutamine in both protected (BOC) and unprotected forms, as shown in the Table. This data demonstrates the ability to add modifications affecting selectivity and membrane impermeability to glutamate analogs while stir retaining, or enhancing, inhibitory activity towards glutaminase.

TABLE 4

Glutaminase Inhibition by
Glutamate Analogs in Brain Membrane Suspension

| Position Modified | Compound | Conc., mM | Glutaminase Activity, % of Control |
|---|---|---|---|
| none | L-glutamic acid[1] | 1.0 | 105 ± 15 (n = 8) |
| | | 3.3 | 113 ± 32 (n = 7) |
| C4 | 4-fluoroglutamic acid[2] | 0.33 | 67 ± 7 (n = 6) |
| | | 1.0 | 30 ± 9 (n = 10) |
| | | 3.3 | 4.2 ± 1.3 (n = 4) |
| | 2,4-diaminopentanedioic acid[3] | 3.3 | 82 ± 7 (n = 4) |
| | | 9.0 | 103 ± 25 (n = 4) |
| | γ-carboxy glutamate[1] | 3.3; 9.0 | 100; 104 |
| | γ-methylene-DL-glutamate[1] | 3.3 | 105 ± 10 (n = 4) |
| | (±)-threo-4-methylglutamate[4] | 3.3; 9.0 | 170; 100 |

TABLE 4-continued

Glutaminase Inhibition by
Glutamate Analogs in Brain Membrane Suspension

| Position Modified | Compound | Conc., mM | Glutaminase Activity, % of Control |
|---|---|---|---|
| C2 | α-methyl-DL-glutamate[1] | 3.3 | 76 |
| | (2S)-α-ethyl glutamic acid[4] | 3.3 | 95 |
| | glutaric acid[1] | 3.3; 9.0 | 89; 75 |
| C2/C3 | (±)-erythro-3-methylglutamate[4] | 3.3; 9.0 | 34; 18 |
| | (±)-threo-3-methylglutamate[4] | 3.3; 9.0 | 91; 7 |
| | β-glutamic acid[1] | 3.3; 9.0 | 84, 73 |
| | | 9.0 | 83, 94 |
| C1 (COOH) | Glu—Lys[1] | 3.3; 9.0 | 96; 93 |
| | Glu—Gly[5] | 3.3; 9.0 | 94; 95 |
| | L-glutamide[1] | 3.3; 9.0 | 99; 96 |
| | Glu—Val[5] | 3.3; 9.0 | 122; 116 |
| | Glu—Thr[5] | 3.3; 9.0 | 124; 123 |
| C5 (COOH) | γ-Glu—Gly[1] | 3.3 | 90 ± 13 (n = 8) |
| | L-glutamate-5-ethyl ester[1] | 3.3; 9.0 | 98; 92 |
| | L-glutamate-5-methyl ester[1] | 3.3 | 105 ± 7 (n = 3) |
| | | 9.0 | 113 |
| NH$_2$ | Asp—Glu[1] | 3.3; 9.0 | 77; 32 |
| | carbobenzoxy-Glu—OH[5] | 3.3; 9.0 | 65; 56 |
| | N-acetyl Asp—Glu[1] | 3.3 | 83 |
| | N-acetyl-DL-glutamate[1] | 3.3 | 92 ± 10 (n = 6) |
| | | 9.0 | 75 ± 10 (n = 6) |
| | pyro-Glu—Ala—Glu[1] | 3.3; 9.0 | 95; 76 |
| | Trp—Glu[1] | 3.3; 9.0 | 99; 86 |
| | Gly—Gly—Glu[5] | 3.3; 9.0 | 101; 87 |
| | Ser—Glu[1] | 3.3; 9.0 | 104; 88 |
| | Gly—Glu[5] | 3.3; 9.0 | 94; 102 |
| | Gly-D-Glu[5] | 3.3; 9.0 | 109; 90 |
| | BOC—Glu—OH[5] | 3.3; 9.0 | 101; 100 |
| | Val—Glu[1] | 3.3; 9.0 | 114; 99 |
| | Met—Glu[1] | 3.3; 9.0 | 111; 98 |
| | N-methyl-DL-glutamate[1] | 3.3; 9.0 | 102; 124 |
| | N-formamino-Glu[1] | 3.3; 9.0 | 89; 127 |
| | Tyr—Glu[1] | 3.3; 9.0 | 110; 118 |
| | Ala—Glu[1] | 3.3; 9.0 | 117; 115 |
| | Arg—Glu[1] | 3.3; 9.0 | 123; 118 |
| | Glu—Glu[1] | 3.3; 9.0 | 130; 141 |
| C4, NH$_2$ | glycyl-4-fluoroglutamate | 0.33 | 94 |
| | | 0.90 | 80 |
| | | 3.3; 9.0 | 55; 30 |
| | BOC-glycyl-4-fluoroglutamate | 3.3; 9.0 | 52; 15 |

Suppliers:
[1]Sigma;
[2]Lancaster Synthesis;
[3]Sigma/Aldrich Library;
[4]Tocris Cookson Inc.;
[5]Bachem A second class of compounds effective as membrane-impermeant inhibitors includes those with one or several highly polar or anionic sites, which are expected to interact with a putative "phosphate site" on glutaminase. This interaction is presumed to be responsible for activation of the enzyme by polyvalent anions. The highly polar site is one having atoms with a high localization of negative charge, such as the oxygen atoms in a NO$_2$ group. The highly polar or anionic site(s) may include, for example, nitro, carboxylate, or various oxides of sulfur or phosphorus, such as sulfate, sulfonate, sulfate, phosphonate, pyrophosphate, etc., and organic esters of these oxides. Membrane impermeability is normally conferred by the polar or ionic groups. In a preferred embodiment, the compound is gem-disubstituted (e.g. 1,1- or 2,2-disubstituted). A particularly preferred compounds is 1,1-dinitrooctane, discussed below. A second portion of the molecule has appreciable hydrophobic character, for example, an aromatic group or, more preferably, an alkyl chain, preferably having at least six carbon atoms, such as the octyl group in 1,1-dinitrooctane. In the absence of such a hydrophobic group, divalent anions are generally observed to activate glutaminase. The compounds described herein, in contrast, are observed to be inhibitors.

Several such gem-disubstituted compounds were evaluated for glutaminase inhibition in homogenized brain membranes, as described above, and showed significant activity, as shown in Table 5. Because such compounds are believed to compete with phosphate, which selectively activates glutaminase, dose-response studies were conducted at different phosphate levels. The results showed that inhibition was reduced in the presence of high phosphate levels; the effect was particularly evident for 1,1-dinitrooctane and 2-(2-dibenzo(a,d)cyclohepten-5-ylidene)-ethyl malonic acid (alternatively named 2-(2-dibenzosuberen-5-ylidene)-ethyl malonic acid), and at higher concentrations of the remaining compounds. This observation suggests that the compound binds at a site responsible for activation of the enzyme by phosphate and/or other polyvalent anions, which is believed to be distinct from the active site which recognizes glutamate and glutamine. Although many receptors and transporters in the body recognize glutamate, the brain/kidney form of glutaminase is unique in being strongly activated by polyvalent anions, such as phosphate. This property of the enzyme serves as one criterion for its identification (Kvamme et al., 1985). The phosphate activated glutaminase has not yet been the subject of extensive drug development, and there are heretofore no potent and specific inhibitors available. Inhibitor compounds which act by competing with phosphate would be expected to be more selective (i.e. in inhibiting conversion of glutamine to glutamate), and cause fewer side effects, than those which act generally at glutamate/glutamine binding sites. Inhibition assays carried out at different 7phosphate levels, as shown, are a useful method of screening for such compounds.

The data in Table 5 also show that, unlike known glutaminase inhibitors believed to compete with phosphate, such as fatty acyl CoA derivatives (Kvamme, 1974), the present compounds, with the possible exception of higher levels of 2-undec-10-enyl malonate, do not activate glutaminase at the higher phosphate level. A biphasic effect was also noted for 1,2,-dinitrooctane at the lower phosphate level.

TABLE 5

Glutaminase Inhibition by Polar/Charged Inhibitors in
Homogenized Brain Membrane at Low and High Phosphate Levels

| | | Glutaminase Activity, % of Control (n = no. of assays) | |
|---|---|---|---|
| Compound | Concn., mM | 4 mM PO$_4^{-3}$ | 170 mM PO$_4^{-3}$ |
| 1,1-dinitrooctane | 3.0 | 79 ± 27 (n = 3) | 64 ± 43 (n = 3) |
| | 1.0 | 24 ± 2 (3) | 95 ± 3 (3) |
| | 0.3 | 51 ± 4 (4) | 88 ± 17 (4) |
| | 0.1 | 77 ± 11 (4) | 96 ± 4 (4) |
| | 0.03 | 89 ± 6 (4) | 96 ± 3 (4) |
| 2,2-dinitropropionate | 3.0 | 84 ± 5 (3) | 98 ± 3 (3) |
| | 1.0 | 102 ± 3 (3) | 99 ± 15 (3) |
| | 0.3 | 105 ± 8 (3) | 102 ± 5 (3) |
| 3,5-dinitrobenzoate | 3.0 | 71 ± 4 (3) | 101 ± 5 (3) |
| | 1.0 | 109 ± 14 (3) | 98 ± 7 (3) |
| | 0.3 | 97 ± 10 (3) | 106 ± 5 (3) |
| 2,4-dinitrobenzoate | 3.0 | 87 ± 1 (2) | 108 ± 3 (2) |
| | 1.0 | 108 ± 0 (2) | 95 ± 0.5 (2) |
| | 0.3 | 94 ± 2 (2) | 98 ± 10 (2) |
| 2-undec-10-enyl malonate | 1.0 | 65 ± 2 (3) | 134 ± 2 (2) |
| | 0.3 | 67 ± 2 (3) | 87 ± 2 (3) |
| | 0.1 | 96 ± 7 (3) | 89 ± 6 (3) |
| 2-(2-dibenzo(a,d)cyclohepten- | 1.0 | 44 ± 2 (3) | 61 ± 4 (3) |

TABLE 5-continued

Glutaminase Inhibition by Polar/Charged Inhibitors in
Homogenized Brain Membrane at Low and High Phosphate Levels

| | | Glutaminase Activity, % of Control (n = no. of assays) | |
|---|---|---|---|
| Compound | Concn., mM | 4 mM $PO_4^{-3}$ | 170 mM $PO_4^{-3}$ |
| 5-ylidene-ethyl)malonic acid | 0.3 | 75 ± 5 (3) | 83 ± 7 (3) |
| | 0.1 | 86 ± 10 (3) | 86 ± 5 (3) |

This compound was also shown to be neuroprotective in cultures of pure (intact) neurons containing 2 mM glutamine (see Newcomb et al., 1997). The cultures were incubated with 0.1, 0.3 and 1.0 mM 1,1-dinitrooctane. Control incubations consisted of the equivalent amount of Tris buffer (pH 8.6) used to solubilize the compound, as shown in Table 6. Glutamate and LDH levels were determined at 8 and 24 hrs. Glutamate levels were determined as described in Example 2, below. LDH was determined using the Boehringer Mannheim Cytotoxicity Determination Kit (Catalog No. 1644793), according to the manufacturer's instructions. Absorbance was measured at 480 nm. Control experiments showed that 1,1dinitrooctane per se had no effect on the LDH assay.

As shown in Table 6, both glutamate and LDH levels were lowered by 30–40% at these time intervals. The effect was greater at lower concentrations, consistent with the biphasic effect noted above.

TABLE 6

Neuroprotective Activity of 1,1-Dinitrooctane

| | | Control | 1,1-Dinitrooctane/Tris | | | Tris | | |
|---|---|---|---|---|---|---|---|---|
| | | | 0.1 mM/ 1 mM | 0.3 mM/ 3 mM | 1 mM/ 10 mM | 1 mM | 3 mM | 10 mM |
| µM glu | 8 h | 152 ± 37 | 96 ± 11 | 102 ± 6 | 100 ± 50 | 137 ± 15 | 135 ± 17 | 141 ± 19 |
| | 24 h | | 139 ± 18 | 126 ± 19 | 156 ± 20 | 257 ± 45 | 277 ± 43 | 282 ± 42 |
| LDH abs. | 8 h | 1.08 ± 0.1 | 0.87 ± 0.13 | 0.99 ± 0.07 | 1.21 ± 0.07 | 1.26 ± 0.17 | 1.19 ± 0.05 | 1.22 ± 0.09 |
| | 24 h | 1.34 ± 0.15 | 1.15 ± 0.15 | 1.23 ± 0.06 | 1.47 ± 0.11 | 1.44 ± 0.24 | 1.43 ± 0.12 | 1.44 ± 0.09 |

Several phosphate-containing compounds showed moderate glutaminase inhibition in the brain membrane assay, i.e. to about 75–90% of control at 3 mM and about 70–85% of control at 9 mM. These included pyridoxal 5-phosphate, 2,5-bis(diethoxyphosphoryl) thiophene, tetrabenzyl pyrophosphate, and tetraisopropyl ethylene diphosphonate.

As noted above, membrane impermeance of a compound is demonstrated by comparison of inhibition in intact and damaged cell cultures. Membrane impermeant compounds suitable for use in the invention are generally unable to inhibit glutaminase activity when applied to live primary cell cultures of neurons or to mixed cultures of neurons and glia, while they are able to inhibit glutaminase when applied to crude membranes derived from such cultures or when applied to cells that have been subjected to a traumatic or damaging event, such as the NMDA model described herein.

Figure 6A:
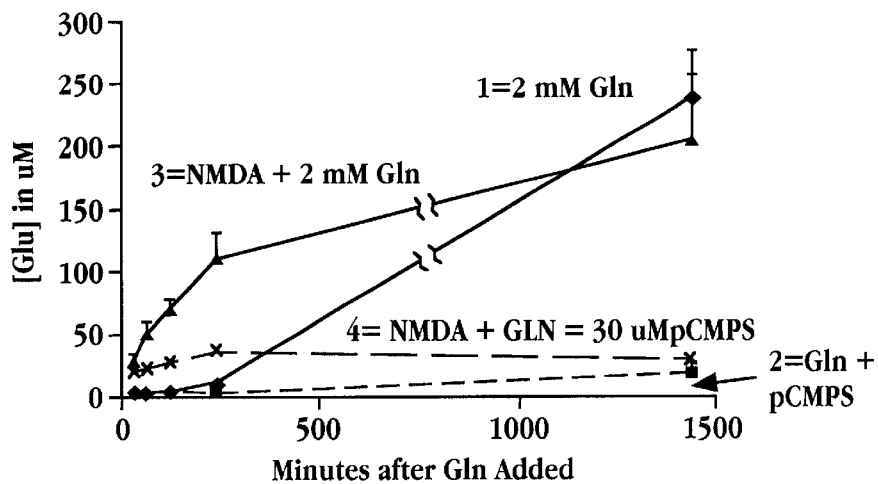
FIGS. 6A and 6B show the effects of pCMPS (p-(chloromercuri)phenyl sulfonic acid) on glutamate production (6A) and LDH release (6B) in pure neuronal cells exposed to NMDA.
Figure 6B:
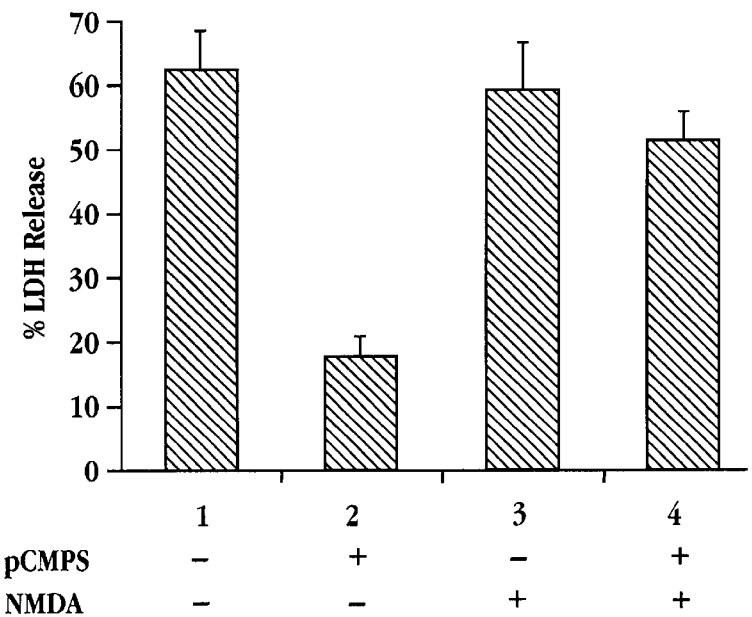

FIGS. 6A–6B show the results of experiments testing the effect of pCMPS, a compound of the first class described above, in intact and damaged neuronal cultures. Pure neuronal cultures were first either incubated under control conditions, or damaged by exposure to NMDA (500 µM, 5 hours). Following this treatment, 2 mM glutamine was added to both sets of cultures, and the effects of 30 µM pCMPS on the resulting generation of glutamate was assayed.

The exposure of healthy neurons to 2 mM glutamine resulted in steadily increasing rates of glutamate generation (FIG. 6A, curve 1). This delayed hydrolysis of glutamine was prevented by the inclusion of 30 µM pCMPS in the culture medium (curve 2). NMDA treatment of neurons resulted in rapid hydrolysis of added glutamine, and this was almost completely inhibited by 30 µM pCMPS (curves 3 and 4, respectively). When added at 600 µM, pCMPS completely abolished glutamate generation by NMDA damaged neurons exposed to cell culture medium and glutamine (not illustrated).

In addition to blocking the gradual increase in glutamine hydrolysis in neuronal cultures exposed to glutamine (FIG. 6A), 30 µM pCMPS also prevented the release of LDH, which is caused by glutamine exposure (FIG. 6B). The neuroprotection by pCMPS in this protocol was verified by morphological assessment, which showed that neurons retained their normal appearance after 24 h in the presence of 30 µM pCMPS and 2 mM glutamine, but were severely damaged if exposed to 2 mM glutamine alone.

The present invention also provides a method for screening for neuroprotective compounds, as demonstrated below. The method is predicated on the observation that useful compounds cannot permeate or are highly resistant to permeation of intact neuronal membranes, but inhibit the glutaminase enzyme present in the membranes of damaged or injured cells. Compounds are tested in a first glutaminase reaction mixture consisting essentially of membranes, particularly mitochondrial membranes derived from central nervous tissue. The reaction mixture also includes about a half-saturating amount of glutamine, usually greater than 0.1 mM, and a glutaminase-activating concentration of phosphate (generally greater than about 0.5 mM). Glutaminase activity in the system is compared in the presence and absence of the test compound. The compound is also tested in a second reaction mixture, prepared by adding the compound to an intact cell membrane preparation at a concentration of between about 0.1 and 2 mM, washing the cells, and then damaging the cells, e.g. by addition of NMDA, and measuring glutaminase activity. The compound is selected for use in neuroprotection if it (i) inhibits glutamate production in the first membrane preparation relative to control, and (ii) does not inhibit glutamate production in the second preparation.

The studies described above show that both pCMPS and the glutamine affinity labels, DON and the Chloroketone, inhibit glutaminase activity in damaged cells. The degree to which glutaminase inhibition is selective to damaged cells was investigated by preincubating neuronal (or mixed) cultures with 30 µM pCMPS, or with 0.5 or 2 mM DON, for 1h, followed by wash and exposure to 500 μM NMDA for 5h. After this period, 2 mM glutamine was added, and glutamate production by glutaminase in the damaged neurons measured over time. The results are presented in Table 7.

TABLE 7

Effects of preincubation of live neurons with DON and pCMPS on increased glutaminase activity after neuronal death.

| Conditions | μM Glu/min |
|---|---|
| Neuronal Cultures | |
| 5h 500 μM NMDA then 2 mM Gln | 0.82 ± 0.10 (s.e.m. n = 7) |
| .25h 30 μM pCMPS then NMDA, then Gln | 0.88 ± 0.13 (7) |
| 1h 30 μM pCMPS then NMDA, then Gln | 0.75 ± 0.07 (7) |
| .25h 2mM DON then NMDA then Gln | 0.23 ± 0.03(7) |
| 1h 2 mM DON then NMDA, then Gln | 0.15 ± 0.02 (7) |

The lack of effect of pCMPS on the glutaminase activity of intact neurons further confirms that the increased glutaminase activity after neuronal death is correlated with membrane breakdown. When combined with the observation of inhibition of glutaminase in damaged neurons by PCMPS, this result serves as proof of concept for using membrane impermeant agents to selectively block only the enzyme in damaged neurons.

The inhibition of glutaminase by DON added to live cells is likely due to efficient transport of DON into mitochondria by a carrier(s) similar or identical to that which transports glutamine (Huber et al. 1988). There are considerable disadvantages to the use of a rapidly transported inhibitor, such as rapid uptake by tissue, and subsequent poor bioavailability, as well as toxicity due to inhibition of multiple enzyme systems: these properties are likely responsible for the toxicity and poor tissue penetration observed by others after CNS administration of DON (Kaneko et at. 1992).

It should be noted that a membrane permeant inhibitor which is reversible could satisfy condition (ii) above by washing out of the cells even after it has first permeated. Therefore, if an inhibitor is suspected to be reversible, it is preferably subjected to further assays. For example, a membrane permeant inhibitor, whether reversible or irreversible, will inhibit glutamate production by live neurons, while a membrane impermeant inhibitor, whether reversible or irreversible, will be inactive. Other assays useful for selecting preferred, that is, membrane impermeant, compounds include effect on synaptic transmission and induction of LDH release, as described further below.

E. Reduced Toxicity of Selective Extracellular Glutaminase Inhibitors

E1. Cellular Toxicity

As mentioned above, an important feature of the present invention is the discovery that selective extracellular glutaminase inhibitors may be administered to reduce the spread of neuronal damage following a traumatic or ischemic insult to the central nervous system. According to an important feature of the present invention, selected compounds exhibit reduced overall toxicity to central nervous tissue, by virtue of their selectivity for extracellular glutaminase. By way of illustration, the relative toxicities of several glutaminase inhibitors have been studied. These studies demonstrate another feature of the compound selection process.

Preliminary studies using the nonselective glutaminase inhibitors 6-diazo-5-oxo-L-norleucine (DON) and L-2-amino-5-oxo-chloropentanoic acid (Chloroketone) showed that both these compounds, when applied at a concentration of 0.5–2 mM to neuronal cells in culture, resulted in release of lactate dehydrogenase from the cells, indicating cellular toxicity and death.

In contrast, 30 μM PCMPS, a membrane impermeant inhibitor, did not cause LDH release from control cultures. The compound was also tested for neuroprotection and inhibition of glutamate production in neuronal injury paradigms in the cells. Experiments involved assay of damage (LDH release) and medium glutamate after incubation of pure neuronal cultures, or hypoxic mixed cultures, with 2 mM glutamine. Data are summarized

TABLE 8

Effect of pCMPS on LDH release and medium glutamate in neuronal cultures exposed to Glutamine

| | hours | μM Glu | % neuronal LDH release |
|---|---|---|---|
| Neuronal cultures | | | |
| 2 mM Gln | 24 | 197 ± 23 (s.e.m. n = 11) | 62 ± 22 (12) |
| +30 μM pCMPS | 24 | 10.3 ± 4 (11) | 17 ± 10.5 (12) |
| Mixed cultures | | | |
| 7 h hypoxia | | | |
| 2 mM Gln | 7 | 2.3 ± 1.1 (15) | 48.5 ± 14.4 (12) |
| 2 mM Gln 30 uM pCMPS | 7 | 1.45 ± 1.0 (15) | 38.5 ± 8.1 (12) |

At 30 μM, pCMPS protected pure neuronal cultures from neuronal damage caused by exposure to glutamine. This effect can be observed by both morphological inspection, as well as by measurement of medium LDH. In addition to being neuroprotective, 30 μM PCMPS prevented the exponentially increasing rate of glutamate production by initially undamaged neurons exposed to glutamine. pCMPS also lowered medium glutamate and release of LDH in mixed cultures exposed to glutamine and hypoxia for 7h. Although this effect is not limited by theory, these results suggest that pCMPS exhibits neuroprotection by blocking the increased glutaminase activity from damaged neurons.

E2. Reduced Effects on Synaptic Transmission

Another facet of potential toxicity is the potential that systemically administered glutaminase inhibitors will interfere with normal synaptic transmission. Since glutaminase activity is part of the normal glutamate production process in glutamatergic neurons, interference with the enzyme could also block such transmission, resulting in toxicity to the system. The studies described in this section provide further evidence for the advantage of using compounds designed in accord with the present invention. Such compounds will have less effect on normal transmission, by virtue of their selectivity for extracellular or exposed glutaminase and attendant inability to enter healthy intact cells.

In studies carried out in support of the present invention, glutamatergic transmission was studied with field potential recordings in the presence or absence of DON or pCMPS. The selectivity of inhibition of glutaminase in damaged vs. intact cells was addressed by measuring glutamatergic transmission in brain slices exposed to either of these compounds.

Figures 7A, 7B:
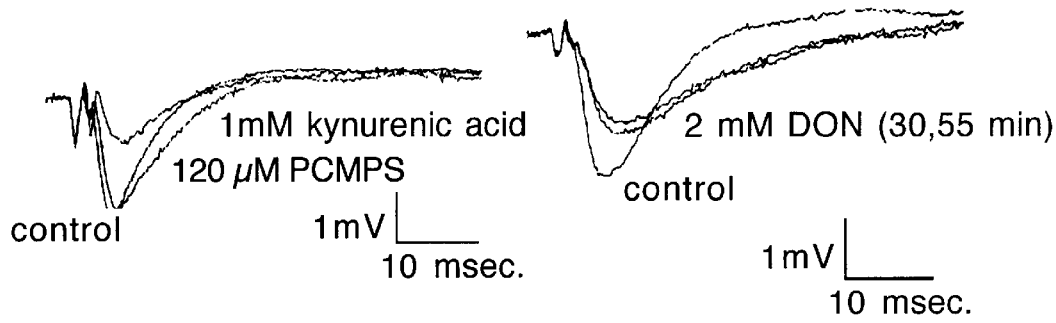
FIGS. 7A and 7B show the effects of pCMPS (7A) and DON (7B) on hippocampal field potentials.

Field potentials were measured as detailed in Example 8. FIGS. 7A and 7B show the effects of DON and pCMPS on hippocampal field potentials. FIG. 7A compares the field potential recorded after 60 min perfusion of 120 µM pCMPS with that recorded prior to perfusion. As a positive control, this Figure also shows effects of subsequent perfusion of 1 mM of the glutamate receptor blocker kynurenate. FIG. 7B shows the effect of 2 mM DON on field potential.

Consistent with the lack of effect of membrane-impermeant inhibitors on glutaminase activity in intact cells, as discussed herein, pCMPS, at a concentration several fold higher than the 10–30 µM required to inhibit glutaminase, had no effect on the field potential. This lack of effect on the field potential demonstrates, in accordance with the present invention, that pathological glutaminase activity can be blocked by an agent which does not interfere with glutamatergic transmission. Perfusion of hippocampal slices with 2 mM DON, in contrast, decreased the magnitude and prolonged the duration of the field potential, indicating that this agent was able to interfere with glutamatergic transmission.

III. Preventing Neuronal Death by Inhibiting Glutaminase

A. Role of Glutaminase Activity in Zones of Damaged Neurons

It is well known that, when a portion of brain tissue is damaged, for example by ischemic insult, the damage may spread over a time period of up to and including about 72 hours following the initial insult. That is, the size and degree of damage can progress over time. Accordingly, studies were carried out in support of the present invention to determine whether augmented extracellular glutaminase activity plays a role in this progression of damage.

One well-established model of cerebral ischemic damage (stroke) is the rat middle cerebral artery occlusion (MCAO) model in which a rat's middle cerebral artery is permanently occluded (Zea Longa et al. 1989), as described in Example 6. According to this protocol, at various time points following the occlusion, brains are taken and histological damage assessed, as detailed in Example 6. Using this approach, in experiments carried out in support of the present invention, lesion areas were defined as "core", or "penumbra" on the basis, respectively of no or partial staining of fresh tissue sections with the dye 2,3,5-triphenyltetrazolium chloride. The tissue was homogenized, and large particulates were removed by a low speed centrifugation. Maximal glutaminase activity was determined in the various regions following addition of excess glutamine (16 mM) and phosphate (115 mM, pH 8.6) to the resulting suspension, and subsequent determination of glutamate over time. Table 9 shows the results of these studies.

TABLE 9

Maximal glutaminase activity in areas of ischemic lesion (data are expressed as mol/min/mg tissue, or approx. mM/min in volume of tissue)

| Time after MCAO | core | penumbra | contralateral |
|---|---|---|---|
| 6 h | 1.25 ± 0.28 | 5.77 ± 1.7 | 8.53 ± 1.5 |
|  | s.e.m. n = 3 |  |  |
| 24 h | 0.30 ± 0.10 | 3.5 ± 1.5 | 8.8 ± 3.8 |
| 48 h | .17 ± 0.12 | 2.1 ± 0.79 | 7.9 ± 0.11 |

Although glutaminase is appreciably inactivated in the core of the ischemic area, significant activity remains in areas of partial, or evolving ischemic damage.

Further studies carried out in support of the present invention measured the composition of extracellular amino acids and the effects of perfusion through dialysis probes of glutamate and phosphate. In these studies, rats were subjected to MCAO, as described above and in Example 6, and were then fitted with in vivo microdialysis probes according to standard methods known in the art (Example 7). Briefly, this method is used to judge neurochemical efficacy in stroke models. In initial experiments, levels of various amino acids, including the amino acid neurotransmitters gamma-amino butyric acid (GABA) and glutamate, were determined in the ischemic penumbra at various times following ischemia. Results of these experiments are presented in Table 10.

TABLE 10

Dialysate composition in ischemic penumbra at 24 h after MCAO (Tau = taurine)
Values are in µM ± s.e.m.; n.d., not determined (Gln is normally 10–20 µM)

| Experiment | Glu | Ser | Gln | Gly | Tau | GABA | Ala |
|---|---|---|---|---|---|---|---|
| Control n = 4 | .97 ± .07 | 4.2 ± .4 | n.d. | 2.4 ± .1 | 3.4 ± .3 | .10 ± .03 | 4.4 ± .7 |
| A 24 h Ischemia n = 4 | 7.0 ± 2.0 | 8.7 ± 4.6 | 11 ± 6 | 4.6 ± 1.2 | 8.2 ± 1.7 | .65 ± .29 | 17 ± 3.6 |
| B 24 h Ischemia n = 3 | 14 ± 6 | 14 ± 4 | 13 ± 7 | 15 ± 5 | 15 ± 5 | 10 ± 6 | 32 ± 13 |

With probes implanted in ischemic penumbra at 24 h, elevated amounts of glutamate (>5 µM) and several other amino acids were observed in all experiments, but amounts of GABA in dialysates were below 1 µM in greater than 50% of animals. The dialysate compositions obtained from ischemic penumbra at 24 h are divided into those in which GABA is below 1 µM (group A), and those in which GABA is significantly elevated (group B). Even in those experiments where GABA is not greatly increased (<1 µM) glutamate is significantly elevated (mean=7 µM). The differential increase in glutamate as opposed to GABA is consistent with formation of extracellular glutamate by a mechanism other than transmitter release in the ischemic penumbra at 24h after occlusion, since it would be expected that if the elevation were due to release of neurotransmitter pools, GABA would also be elevated. As shown, significant amounts of the glutaminase substrate, glutamine, continued to be present in the dialysate of the ischemic penumbra at 24 h after MCAO. Since plasma is generally very low in glutamate, these results suggest that the dialysate glutamate originates in the brain.

In further microdialysis experiments, exogenous glutamine was added to the ischemic penumbra via the probe, and dialysis glutamate was measured, as described in Example 7. When 10 mM glutamine plus 20 mM sodium phosphate were perfused into the penumbra for one hour, dialysate glutamate was elevated 315% as compared to control (±115%). Subsequent perfusion of phosphate further increased dialysate glutamate to 845% of control (±400%). The effects on glutamate were much more pronounced than on other amino acids measured; therefore, these studies provided further support for the involvement of extracellular glutaminase activity in producing the elevated levels of glutamate in cortical tissue undergoing ischemic damage.

B. Reduction of Neuronal Damage in vivo

The foregoing test paradigms are also used to assess the ability of test compounds to reduce neuronal damage in vivo. That is, using the MCAO model as an example, animals subjected to MCAO and fitted with a microdialysis probe in the affected brain region are given a test glutaminase compound through the probe. Glutamate production is measured, as described above, and a compound is considered to be potentially neuroprotective if it attenuates the above-described rise in glutamate in the ischemic penumbra region.

Further tests are made giving the test compound systemically, as this mode of administration is contemplated for use in the treatment of mammalian subjects. That is, a compound is given systemically, typically intravenously, to test animals who have undergone neuronal insult, such as ischemic insult to the central nervous system, as discussed above. The compound is administered in a pharmaceutically acceptable vehicle, preferably and aqueous vehicle, such as normal or buffered saline. Selected brain regions are then assessed for presence of absence of neuronal damage, usually by any of a number of histological techniques known in the art. Appropriate models of neuronal insult, including models of cerebral ischemia, such as the MCAO model referred to herein, are known in the art. The amount and statistical significance of the reduction required to consider a test compound suitable for clinical use are parameters which are well within the skill of practitioners in the art of clinical assessment. Dose-response studies, which are likewise within the knowledge and judgment of skilled practitioner, can be used to establish adequate dosing ranges for experimental treatment paradigms, as well as to extrapolate such doses to use in larger animals, including humans.

According to an important feature of the present invention, neuroprotective compounds in accordance with the present invention will optimally have low cell membrane permeability. While such a characteristic is also generally associated with poor penetration through the relatively impenetrable capillary epithelial junctions that constitute the so-called blood-brain barrier, administration of such compounds to the central nervous system is not considered to be a significant obstacle. First, it is now known that when there is injury to the brain, the blood brain barrier breaks down to allow penetration of membrane impermeant compounds. It is now well established that blood brain barrier breakdown accompanies neural injury. This is shown by significant edema and retention of membrane impermeant contrast agents used for various imaging techniques. Since a membrane impermeant glutaminase inhibitor should behave in the same way as such a contrast agent, blood brain barrier passage is not a problem with these compounds.

Second, direct administration to the affected region, such as by intracerebroventricular or intrathecal delivery routes or direct shunt, are also possible in the context of the present invention.

EXAMPLES

The following examples illustrate, but in no way are intended to limit the present invention.

Materials and Methods

The cell culture used was Eagle's Minimal Essential Medium, containing 1 mM phosphate (bicarbonate-free and glutamine-free), purchased from Gibco BRL (Rockville, Md.). Horse and fetal bovine serum were obtained from Hyclone Laboratory Inc. (Utah). All other tissue culture reagents were from Sigma Chemical Co. (St. Louis, Mo.).

Primary cultures of cerebral cortical cells were prepared from Swiss Webster mice (Simonsen Laboratories) All animal use procedures were in strict accordance with the National Institutes of Health Guide for Care and Use of Laboratory Animals.

Cultures of pure cortical neurons and mixed cultures of neurons and astrocytes were prepared by modifications of published procedures (Dichter, M. A. (1978) Brain Res. 149, 279–203; Choi, D. W. et al. (1987) J. Neurosci. 7, 357–368; Dugan, L. L. et al. (1995)J. Neurosci. 15, 4545–4555).

Astrocytes were cultured from cortical cell suspensions from 1–2 day old Swiss Webster mouse pups. Mixed cultures of neurons and astrocytes were obtained by plating cortical neurons from embryonic day 15–16 mice on confluent astrocyte monolayers. Pure neuronal cultures were made from the same embryonic cortical cell suspensions; astrocyte growth was inhibited by adding cytosine arabinoside and decreasing serum in the medium. For survival, neuronal cultures were fed with glial conditioned medium. Neuronal cultures were used for experiments at 11–15 days in vitro, and mixed cultures at 13–15 days after plating the neurons.

Glutamine was purchased from Bachem or from Gibco. In order to avoid possible complications from glutamate toxicity, glutamate was removed from the Bachem glutamine by passage of a 50 mM solution over a x100 cm column of Diethylaminoethyl Sepharose (Pharmacia Fine Chemicals, Piscataway, N.J.) at pH 5.0. The resulting glutamine stock contained less than 0.2 $\mu$M glutamate in a 2 mM solution, and was used in the experiments with the pure neurons, and to show glutamine toxicity in hypoxic mixed cultures. Glutamine obtained from Gibco BRL (Rockville, Md.) contained 1–2 $\mu$M glutamate in a 2 mM solution, and was used in some of the experiments with the mixed cultures (where the small amount of added glutamate is rapidly removed). Glutamine solutions were stored at concentrations of 50 mM or greater at −20° C.

Statistical procedures: All data are expressed as the mean and the standard error of the mean. Each n represents data from one culture well. Where not given in the text, values for n are given in the tables. Unless otherwise indicated, an n of 4–6 culture wells was used for each condition in each experiment, with repetitions carried out using at least 3 independent dissections for each experiment. Statistical comparisons were performed by the standard t-test for the comparison of the means of two populations.

EXAMPLE 1

Exposure of Cells to Hypoxic Conditions

Hypoxia was carried out at 37° C. in an anoxic chamber (<0.2% oxygen; Forma Scientific). Before each experiment, the medium was pre-equilibrated with an anoxic gas mixture containing 5% $CO_2$, 85% $N_2$ and 10% $H_2$ and incubated at 37° C. Cells were deprived of oxygen by triple exchange (approximately 1:1000 dilution) of the culture medium with deoxygenated Minimal Essential Medium (MEM; Sigma), with or without the addition of glutamine to the indicated concentration. The oxygen tension in the anoxic chamber was monitored using an oxygen electrode (Model MI-730; Microelectrodes Inc.). After 5 or 7 h of hypoxia, the cultures were returned to the normoxic incubator.

EXAMPLE 2

Determination of Glutamate and Glutamine Concentrations and Production Rates in Cell Cultures Pre-column derivatization with o-phthalaldehyde (OPA, Sigma) and separation by reversed phase HPLC was used. A Gilson HPLC was fitted with a Hewlett-Packard model 1046A fluorimetric detector (excitation 340 nm, emission 420 nm). Medium was collected from cell culture at various times, and frozen at −80° C., prior to dilution of 5 or 10 $\mu$l into auto-sampler vials containing 40 or 45 $\mu$l dimethylformamide:water 1:3 (derivatives with 2-mercaptoethanol) or 1:9 (derivatives with N-acetyl-L-cysteine). For analysis of the derivatives formed with 2-mercaptoethanol, samples were reacted according to published methods (Newcomb, R. (1989) LC GC 7, 570–578; Lindroth, P., and Mopper. K., (1979) Anal. Chem. 51, 1667–1674.), and a gradient of 0–40% methanol in 1.25 mM sodium phosphate pH 6.2 over 20 min was used to elute the derivatives from a 4.5×250 mm Beckman Ultrasphere octadecylsilica column (dp 5 $\mu$m) at 1 ml/min. For analysis of the derivatives formed with N-acetyl-L-cysteine (Bruckner), samples were reacted with 25 $\mu$l of 1 mg/ml OPA, and 50 $\mu$l of 1 mg/ml N-acetyl-L-cysteine (Fluka) in 0.5 M potassium borate pH 10.0. Chromatography was carried out on a 4.5×250 mm Phenomonex Primesphere "HC" octadecylsilica column (dp 5 $\mu$m) using a gradient of 0–35% methanol in 15 mM sodium phosphate pH 6.2 (0.13% tetrahydrofuran) over 65 minutes at 1 ml/min. It was shown for each of the experimental conditions (ie. glial and control and damaged neuronal and mixed cultures) that both analytical systems gave results for glutamate and glutamine measurements which were, within error, identical.

Glutamate concentrations were converted to units of pmol/$\mu$l of culture medium, or $\mu$M. In the absence of cellular uptake (ie, in damaged neuronal cultures), the rate of glutamate production was obtained directly from the measurements of the amounts of glutamate in culture medium at various times.

Experiments on the clearance of glutamate from culture medium showed first order kinetics in intact glial, neuronal, and mixed cultures. This allows expression of medium glutamate concentrations as:

$$d[Glu]/dt = S - k[Glu] \quad (1)$$

where [Glu], in units of $\mu$M, is the concentration of glutamate in the 0.4 ml of medium in a culture well, S (in $\mu$M/min) is the rate of addition of glutamate to the culture medium from cellular sources, and k (in min$^{-1}$) is the empirically determined rate constant for clearance (Roberts, D. V. (1977) Enzyme Kinetics, Cambridge University Press, Cambridge, pp23–30.). Pseudo-first order kinetics are expected for the clearance of glutamate at concentrations significantly below the Km for cellular uptake (about 45 $\mu$M; Hertz, L. et al. (1978) Neurochem. Res. 3, 1–14; Drejer, J. et al. (1982) Exp. Brain Res. 47, 259–269.). Although the value of k is proportional to cell (carrier) density, little variation is expected in cultures containing glia as glial cultures are confluent.

In cultures where glutamate concentrations are (within error) constant, d[Glu]/dt is close to zero, and cellular production of medium glutamate is balanced by its removal, such that glutamate production can be calculated from the steady state equation:

$$S = k[Glu] \quad (2)$$

Calculations were performed using the slopes of the regression lines which describe the rate constants for glutamate removal and the mean values for culture medium glutamate concentrations. Because of the relevance to data on glutamate toxicity, rates of glutamate production are given with units of concentration over time. For comparative purposes, glutamate production rates can be expressed as pmol of glutamate produced per min in each culture. These values were obtained after multiplication by the volume of culture medium.

Measures of culture medium and total cellular lactate dehydrogenase activity (see Example 3, below) were performed for all experiments, and were used to verify that systematic variations in neuronal density did not affect the results: essentially identical results were obtained for data in Tables 1–3 if normalized to mean total culture LDH release. The mean of the total neuronal LDH was 259 units with pure neuronal cultures (n=116), and 776 units with the mixed cultures (n=99). The coefficient of variation of the LDH measurements was 0.38 in both culture systems.

EXAMPLE 3

Measurement of Neuronal Death

For studies in which cells were injured by exposure to the glutamate antagonist NMDA, cell cultures were incubated with 500 $\mu$M NMDA for 5 h in culture medium, followed by wash and addition of phosphate free saline (116 mM NaCl, 5.4 mM KCl, 5 mM magnesium sulfate, 1.8 mM calcium chloride, 14.7 mM sodium bicarbonate, 10 mM HEPES buffer, pH 7.4) with or without 2 mM Glutamine, 20 mM phosphate, and/or 2 mM DON. Glutamate hydrolyzing (glutaminase) activity was measured as described in Example 2. For localization of the activity of the glutaminase, medium was removed from cells, and fresh medium was then added to the remaining cell layer. Glutamine (2 mM) was added to both cells and the isolated medium, followed by removal of aliquots at various times for determination of medium glutamate. At the end of the experiment, both the cell and medium samples were subjected to freeze-thaw, and LDH activity was measured.

Neuronal death was measured by assay of lactate dehydrogenase (LDH) activity released into the culture medium according to standard procedures (Koh et al. (1987) J. Neurosci. Meth. 20, 83–90.). Cell viability was also independently assessed by light microscopy for all experiments. The amount of LDH released was expressed as the ratio of LDH activity in the medium to the amount released from the same cultures after induction of complete neuronal death at the end of the experiment. In mixed neuronal-glial cultures, total neuronal LDH was defined as enzyme released after 24 h exposure to 500 $\mu$M NMDA. In neuronal cultures, neuronal LDH release was measured after freeze-thaw. In the neuronal cultures, LDH release by the NMDA exposure method is normally about 85 % of that obtained by freeze thaw.

EXAMPLE 4

Western Blot Analysis of Cell Cultures

Neuronal cultures were exposed to 500 $\mu$M NMDA or control conditions for 5 hours, at which time the medium was removed from the cellular layer and both were stored at −80° C. The media from single wells (300 μl) were centrifuged at 100,000×g for 40 min. The resulting pellets were resuspended in 40 μl of sample loading buffer and subjected to SDS-gel electrophoresis. The cells from a single well were resuspended in 100 μl of sample loading buffer and 20 μl were used. Gel electrophoresis and Western blotting was performed as described by Srinivasan et al. (Srinivasan, M., Kalousek, F., and Curthoys, N. P. (1995) J. Biol. Chem. 270, 1185–1190) except that the immune complex was detected using the Enhanced Chemiluminescence System (Amersham). The relative intensities of the resulting bands were determined by densitometric analysis using a Microscan 2000 Densitometer.

EXAMPLE 5

Glutaminase Inhibition Assay

Membranes are prepared by homogenization of brain tissue in 330 mM sucrose, 20 mM Tris acetate (pH 7.4) and 1 mM EDTA, using approx. 10 g tissue/150 ml homogenization solution. After a low speed spin (1000 G for 5 min), the membranes are pelleted at 17000 G (10 min) and stored at −80° C. For assays, 50μl of the pellet was diluted into 10 ml of 330 mM sucrose/ 20 mM Tris acetate (pH 8.6). To about 80μl of this suspension were added stock solutions of sodium phosphate (pH 8.5) and glutamine (purified by passage over DEAE-Sepharose to remove glutamate), sufficient to give final concentrations of 7 mM phosphate and 1.8 mM glutamine, in about 120 μl total volume. These amounts of substrate (glutamine) and activator (phosphate) are near the concentrations of half maximal effects, and also close to that expected in damaged brain. Test compounds were generally dissolved in 30% DMSO at 100 mM. Highly charged compounds, such as phosphate and nitro compounds, were dissolved in 1M Tris acetate (pH 8.6) at the same concentration. The solutions were then diluted to the concentrations shown in Tables 3–4. Detection of glutamate formation is performed at periodic intervals by reverse phase HPLC after derivatization with o-phthaldialdehyde and thiol (see Example 2). Results, relative to control (vehicle only, without inhibitor) are given in Tables 3–4.

EXAMPLE 6

Assessment of Damage following Middle Cerebral Artery Occlusion

Rats were subjected to middle cerebral artery occlusion, according to standard methods (Zea Longa et al., 1989). Test rats are sacrificed at 6, 24 and 48 h after occlusion. Sections of approximately 1 mm were cut, and lesions defined by tetrazolium chloride (TTC) staining of alternate sections. Lesion areas were defined as "core" (no TTC staining, or tissue remaining white) or "penumbra" (partial TTC staining, or tissue stained pink; vs. the normal deep red), and regions of approximately 3×4 mm were dissected. Freshly dissected tissue was homogenized (in 400 μl of 330 mM sucrose, 20 mM Tris, pH 8.6), and large particulates removed by a low speed spin. Maximal glutaminase activity was determined following addition of excess glutamine (16 mM) and phosphate (115 mM, pH 8.6) to the resulting suspension, and subsequent determination of glutamate over time (by reversed phase HPLC after derivatization with 2-mercaptoethanol and o-phthaldialdehyde, as described in EXAMPLE 2.

EXAMPLE 7

Use of in vivo Microdialysis to Assess Biochemical Changes as a Consequence of MCAO in Rats The middle cerebral arteries of rats were occluded as in EXAMPLE 7, and the rats were returned to their cages overnight. The next morning, dialysis probes (.0.5 m diameter, 2 mm length, 20,000 dalton cutoff) were inserted into ischemic penumbra (cortex) and perfused with artificial CSF at 3 μl/min for 1 h prior to collection of 10 minute fractions of dialysate. The effectiveness of the occlusion and the placement of probes were verified by TTC staining of 1 mm sections at the conclusion of the experiment. Amino acids in the dialysate were measured by reverse phase HPLC with fluorescence detection, after derivatization of the dialysates with o-phthaldialdehyde and N-acetyl-L-cysteine Following a 1 h stabilization after implantation of probes into the ischemic penumbra (at 24 h post occlusion), the basal dialysate was collected for 1 h. In three animals, this was followed by a 1 h perfusion through the probe of 10 mM glutamine, and a subsequent 1 h perfusion of 10 mM glutamine with 20 mM sodium phosphate (pH 7.4; substituted for sodium chloride in the artificial CSF).

EXAMPLE 8

Measurement of Field Potentials from Hippocampal Slices

A bipolar extracellular stimulating electrode was placed in the Schaffer/commissural fibers in the CA2 region of 400 μm hippocampal slices taken from 100–120 g rats. Slices were maintained at 34° C. in oxygenated Krebs-Ringer saline. Population EPSPs were elicited at low frequency (0.1 Hz), recorded with an extracellular electrode placed in stratum radiatum of the CA1 subfield, and digitized at 5 Hz with a microcomputer. Following stabilization (1 h), baseline data were obtained prior to application of 2 MM DON or 120 μM pCMPS (10 sweeps) and 5 sweeps were sampled at at 5 min intervals for 1 h following perfusion of the test compound. Where an effect was observed (DON), this was stable after about 15 min of perfusion. Experiments were replicated 2–4 times, with similar results.

EXAMPLE 9

Preparation of Glycyl-4-fluoroglutamate

BOC-Gly-OH (0.35 μmol) was dissolved in 200 ml DMF and reacted with 1 eq HBTU (2-(1-hydroxy-benzotriazol-1-yl)-1,1,3,3-tetramethyluronium hexafluorophosphate) and 2 eq DIEA (diisopropylethylamine). After 10 min, the mixture was added to 0.3 μmol 4-fluoro-Glu-OH in 1.4 ml dioxane/water (7:3) containing 2 eq NaOH. After 1 hr, the solvent was removed by evaporation, and the residue was acidified with HCl and purified by reverse phase HPLC on an octadecyl silica support, eluting with a gradient of methanol in 0.1 % aqueous trifluoroacetate. The BOC protecting group was removed from a portion of the product by treating with trifluoroacetic acid for 1 hr.

While the invention has been described with reference to specific methods and embodiments, it will be appreciated that various modifications and changes may be made without departing from the invention.

It is claimed:

1. A method of reducing damage to neuronal cells in a neuronal tissue of a subject who has experienced neuronal injury, comprising administering to the subject, in an amount effective to reduce such damage, a compound which selectively inhibits extracellular glutaminase relative to glutaminase present in intact cells, wherein said compound is impermeable to intact cell membranes, such that said compound does not inhibit glutaminase when contacted with live intact cell cultures of neurons and glia, and inhibits glutaminase when applied to crude membranes derived from said cell cultures.

2. The method of claim 1, wherein said neuronal injury is the result of an ischemic event that occurs in the central nervous system.

3. The method of claim 2, wherein said subject has experienced a focal cerebral ischemic event.

4. The method of claim 1, wherein said compound comprises a reactive portion having a chemical affinity for the active site of glutaminase.

5. The method of claim 4, wherein said compound is a glutamate analog.

6. The method of claim 5, wherein said glutamate analog is derived from 4-fluoroglutamate, glycyl-4-fluoroglutamate, or 3-methylglutamate.

7. The method of claim 6, wherein said glutamate analog is derived from 4-fluoroglutamate.

8. The method of claim 4, wherein said reactive portion is a thiol-reactive moiety.

9. The method of claim 8, wherein said compound is p(chloromercuri) phenylsulfonic acid.

10. The method of claim 1, wherein said compound is further characterized by a selectivity for brain/kidney glutaminase with respect to a glutamine-utilizing protein selected from the group consisting of amidotransferases and gamma-glutamyltranspeptidase, such that said compound inhibits said brain/kidney glutaminase by 50% at a concentration that is at most $1/10$ of a concentration effective to inhibit said glutamine-utilizing protein by 50 %.

11. The method of claim 2, wherein said compound is administered to said subject at least two hours after said ischemic event.

12. The method of claim 11, wherein said compound is administered to said subject at least six hours after said ischemic event.

13. The method of claim 1, wherein said neuronal injury is the result of trauma to the central nervous system.

14. The method of claim 1, wherein said neuronal injury is the result of a chronic neurodegenerative disorder.

15. The method of claim 14, wherein said chronic neurodegenerative disorder is Alzheimer's disease.

16. The method of claim 1, wherein said compound is able to cross the blood-brain barrier after said neuronal injury but is substantially unable to be taken up by neuronal cells.

* * * * *